(12) United States Patent
Tanabe et al.

(10) Patent No.: US 9,668,650 B2
(45) Date of Patent: Jun. 6, 2017

(54) OPHTHALMOLOGIC APPARATUS

(71) Applicant: KABUSHIKI KAISHA TOPCON, Itabashi-ku (JP)

(72) Inventors: Takao Tanabe, Itabashi-ku (JP); Ikuo Ishinabe, Saitama (JP); Kazuhiro Omori, Setagaya-ku (JP); Takuji Sato, Suginami-ku (JP)

(73) Assignee: KABUSHIKI KAISHA TOPCON, Itabashi-ku (JP)

( * ) Notice: Subject to any disclaimer, the term of this patent is extended or adjusted under 35 U.S.C. 154(b) by 5 days.

(21) Appl. No.: 14/681,403

(22) Filed: Apr. 8, 2015

(65) Prior Publication Data

US 2015/0282707 A1    Oct. 8, 2015

(30) Foreign Application Priority Data

Apr. 8, 2014 (JP) ................... 2014-079575
Apr. 2, 2015 (JP) ................... 2015-075715

(51) Int. Cl.
| | |
|---|---|
| *A61B 3/14* | (2006.01) |
| *A61B 3/12* | (2006.01) |
| *A61B 3/10* | (2006.01) |
| *A61B 3/103* | (2006.01) |

(52) U.S. Cl.
CPC ............ *A61B 3/1225* (2013.01); *A61B 3/102* (2013.01); *A61B 3/103* (2013.01); *A61B 3/14* (2013.01)

(58) Field of Classification Search
USPC ........................................................ 351/206
See application file for complete search history.

(56) References Cited

U.S. PATENT DOCUMENTS

| | | |
|---|---|---|
| 5,815,242 A | 9/1998 | Anderson et al. |
| 2010/0141895 A1 | 6/2010 | Cairns et al. |
| 2013/0335703 A1 | 12/2013 | Creasey et al. |
| 2015/0216408 A1 | 8/2015 | Brown et al. |

FOREIGN PATENT DOCUMENTS

| | | |
|---|---|---|
| EP | 2 903 498 A1 | 8/2015 |
| JP | 5330236 | 10/2013 |
| WO | WO 2014/053824 A1 | 4/2014 |

OTHER PUBLICATIONS

Combined United Kingdom Office Action and Search Report issued Sep. 21, 2015 in Patent Application No. GB1505970.2.

*Primary Examiner* — Jack Dinh
(74) *Attorney, Agent, or Firm* — Oblon, McClelland, Maier & Neustadt, L.L.P.

(57) ABSTRACT

An ophthalmologic apparatus includes a two-dimensional scanning optical system, a refractive optical system, and a concave mirror. The two-dimensional scanning optical system deflects light from a light source in a first angle range. The refractive optical system deflects the light deflected by the two-dimensional scanning optical system in a second angle range that is wider than the first angle range. The concave mirror includes a reflective surface in at least part of the rotational symmetry surface, and reflects the light emitted from the refractive optical system. The exit-side optical axis of the refractive optical system substantially coincides with the rotational symmetry axis of the rotational symmetry surface. The pupil location in the refractive optical system and the exit focus of the concave mirror are located at optically conjugate positions or in the vicinity of the positions. The exit focus is located at a subject's eye position.

19 Claims, 16 Drawing Sheets

OPHTHALMOLOGIC APPARATUS

CROSS-REFERENCE TO RELATED APPLICATION

This application is based upon and claims the benefit of priority from Japanese Patent Application No. 2014-079575, filed Apr. 8, 2014 and Japanese Patent Application No. 2015-075715, filed Apr. 2, 2015; the entire contents of which are incorporated herein by reference.

FIELD

Embodiments described herein relate generally to an ophthalmologic apparatus for acquiring an image of a subject's eye.

BACKGROUND

Examples of ophthalmologic apparatuses include optical coherence tomography (OCT) for acquiring tomographic images, fundus cameras for capturing images of the eye fundus, scanning laser ophthalmoscopes (SLO) that capture images of the eye fundus by laser scanning using a confocal optical system, and slit lamps that shine a thin sheet of light into the cornea to acquire images.

As described above, the SLO is one of the ophthalmologic apparatuses. The SLO scans the eye fundus with lasers and detects return light therefrom with a light receiving device to thereby form the front image of the eye fundus. The SLO is useful for ophthalmic disease screening.

DETAILED DESCRIPTION

Figure 1:
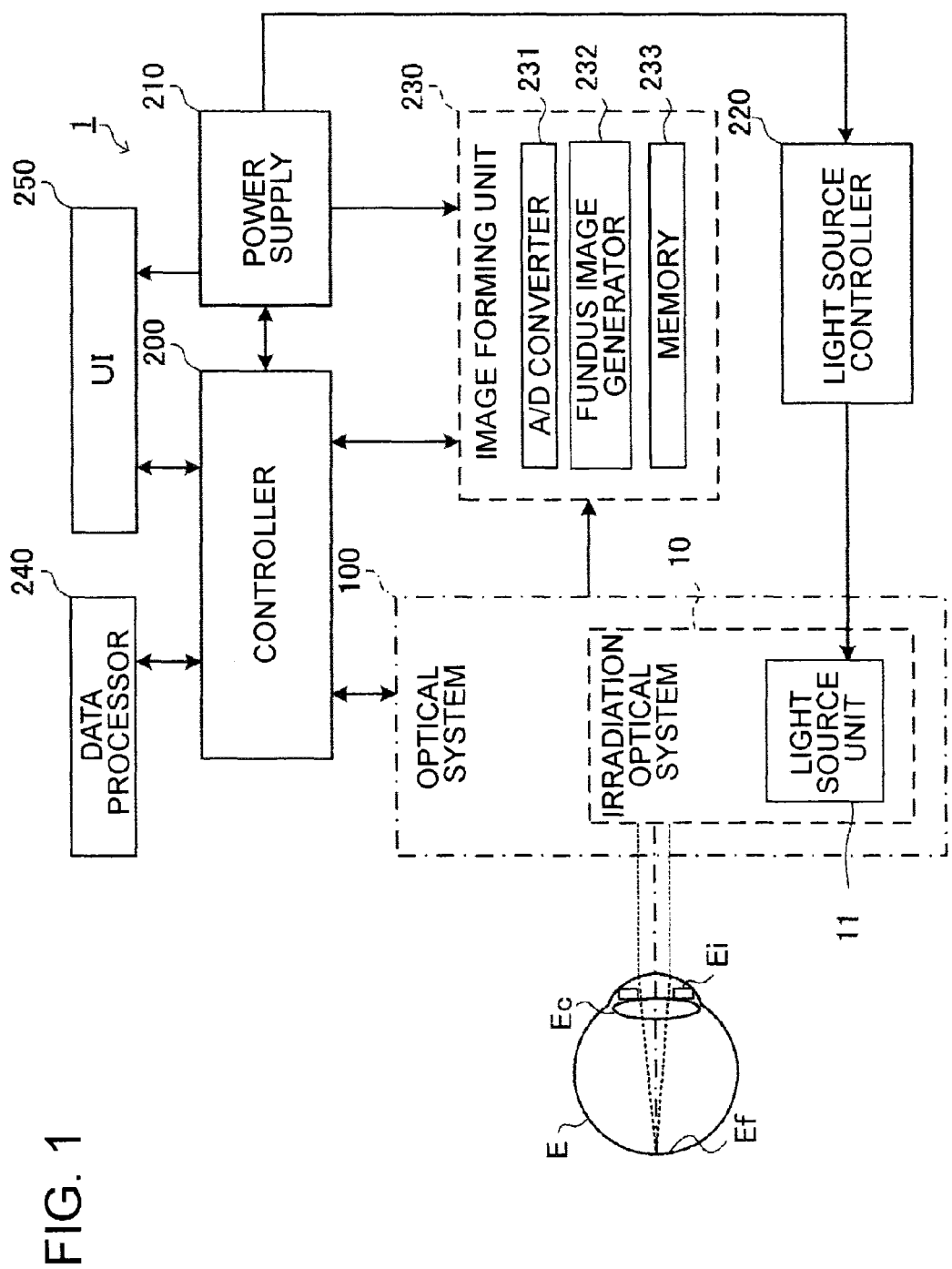
FIG. 1 is a functional block diagram illustrating an example of the configuration of an ophthalmologic apparatus according to a first embodiment.

In general, according to one embodiment, an ophthalmologic apparatus includes a two-dimensional scanning optical system, a refractive optical system, and a concave mirror. The two-dimensional scanning optical system deflects light from a light source in a first angle range. The refractive optical system deflects the light deflected by the two-dimensional scanning optical system in a second angle range that is wider than the first angle range. The concave mirror includes a reflective surface in at least part of the rotational symmetry surface, and reflects the light emitted from the refractive optical system. The exit-side optical axis of the refractive optical system substantially coincides with the rotational symmetry axis of the rotational symmetry surface. The pupil location in the refractive optical system and the exit focus of the concave mirror are located at optically conjugate positions or around the positions. The exit focus is located at a subject's eye position.

Referring now to the drawings, a detailed description is given of an ophthalmologic apparatus according to several embodiments. The ophthalmologic apparatus scans a subject's eye to thereby capture an image of the subject's eye (in particular, eye fundus). Examples of such ophthalmologic apparatus include OCTs for acquiring tomographic images, SLOs that capture the front image of the eye fundus by laser scanning using a confocal optical system, and multifunctional products having functions of OCT and SLO combined together. In the following embodiments, the ophthalmologic apparatus is described as, for example, having functions of SLO.

First Embodiment

Configuration

Figure 2:
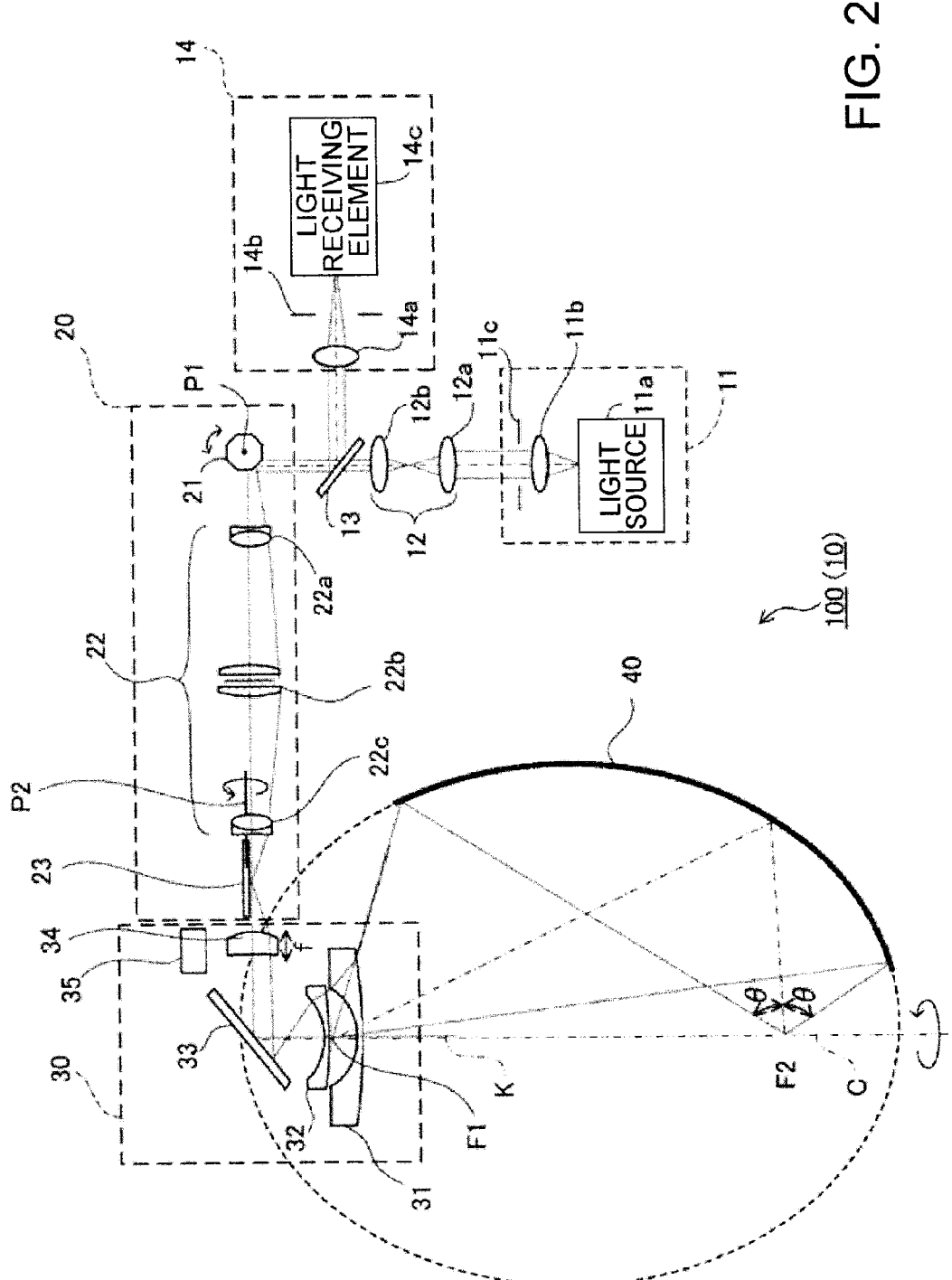
FIG. 2 is a schematic diagram illustrating an example of the configuration of an optical system in the first embodiment.

FIG. 1 is a functional block diagram schematically illustrating the configuration of an ophthalmologic apparatus 1 according to a first embodiment. FIG. 2 is a schematic diagram illustrating the configuration of an optical system 100 illustrated in FIG. 1. Like reference numerals refer to like parts in FIGS. 1 and 2.

The ophthalmologic apparatus 1 scans the eye fundus Ef of a subject's eye E with laser light to acquire data thereon, and forms the front image of the eye fundus Ef based on the data. The ophthalmologic apparatus 1 includes the optical system 100 and a processing system other than the optical system 100. The optical system 100 is used for optical observation and measurement of the eye fundus Ef. The processing system is used for processing data acquired by the optical system 100, controlling each unit in the apparatus, and the like.

Optical System

The optical system 100 includes a various types of optical elements and optical devices as well as mechanisms for a variety of operations. In this embodiment, the optical system 100 includes an irradiation optical system 10. The irradiation optical system 10 includes a light source unit 11. The irradiation optical system 10 guides light from the light source unit 11 to a subject's eye position where the subject's eye E is located. The irradiation optical system 10 receives the light reflected from the subject's eye E to acquire the front image of the eye fundus Ef.

As illustrated in FIG. 2, the irradiation optical system 10 includes the light source unit 11, a beam expander 12, a beam splitter 13, a light receiver 14, a two-dimensional scanning optical system 20, a refractive optical system 30, and a concave mirror 40.

Light Source Unit 11

The light source unit 11 outputs laser light to illuminate the subject's eye position. The light source unit 11 includes a light source 11a, a collimate lens 11b, and an aperture stop 11c. The light source 11a outputs laser light with high spatial coherency. Examples of the light source 1a include semiconductor laser light sources (swept source lasers, super luminescent diodes, etc.), solid-state lasers, and gas lasers. In addition, output light of such light source coupled with an optical fiber, fiber laser, and the like may also be used as the light source 11a.

The collimate lens 11b collimates laser light output from the light source 11a into a parallel flux. The collimate lens 11b may be a compound device made of a combination of the same or different types of optical elements. The aperture stop 11c confines the parallel flux of laser light from the collimate lens 11b to a predetermined range. The parallel flux of laser light confined by the aperture stop 11c is then incident on the beam expander 12.

Beam Expander 12

The beam expander 12 changes the diameter of the flux of laser light output from the light source unit 11. The beam expander 12 includes biconvex lenses 12a and 12b. The biconvex lenses 12a and 12b are located on the optical axis of the laser light output from the light source unit 11. The beam expander 12 changes the diameter of the parallel flux of laser light to a predetermined diameter.

The beam splitter 13 is located between the beam expander 12 and the two-dimensional scanning optical system 20. That is, the beam expander 12 and the two-dimensional scanning optical system 20 are located in the transmission directions of the beam splitter 13. The light receiver 14 is located in the reflection direction of the beam splitter 13.

Light Receiver 14

Light from the two-dimensional scanning optical system 20 is incident on the beam splitter 13. The light receiver 14 receives the return light reflected from the beam splitter 13. The return light is the laser light that has been guided to the subject's eye position and returned therefrom. The return light travels back from the eye fundus Ef of the subject's eye E through the concave mirror 40, the refractive optical system 30, and the two-dimensional scanning optical system 20 in this order. The light receiver 14 includes a condenser lens 14a, a confocal pinhole 14b, and a light receiving element 14c.

The condenser lens 14a focuses the return light reflected from the beam splitter 13. The return light focused by the condenser lens 14a is confined to a predetermined range by the confocal pinhole 14b and detected by the light receiving element 14c. The confocal pinhole 14b is located in a position optically conjugate to the eye fundus Ef of the subject's eye E. The light receiving element 14c has sensitivity in the visible region and the infrared region according to the wavelength of laser light output from the light source 11a. The light receiving element 14c may be, for example, avalanche photodiode. A detection signal obtained by the light receiving element 14c is fed to an image forming unit 230 (described later).

Two-dimensional Scanning Optical System 20

The flux of laser light with a diameter changed by the beam expander 12 passes through the beam splitter 13 and is incident on the two-dimensional scanning optical system 20.

The two-dimensional scanning optical system 20 deflects the light form the light source unit 11 in a first angle range. The two-dimensional scanning optical system 20 includes a polygon mirror 21, a beam expander 22, and a rotating mirror 23.

The polygon mirror 21 is used for vertical scanning by reflecting the laser light output form the light source unit 11. The polygon mirror 21 has a plurality of reflective surfaces each arranged substantially in parallel to a first rotation axis P1, and is rotatable about the first rotation axis P1. The first rotation axis P1 is arranged perpendicular to the optical axis of the laser light output form the light source unit 11. The polygon mirror 21 is arranged such that its reflective surfaces are irradiated with the laser light output form the light source unit 11 at a predetermined rotational position about the first rotation axis P1. The laser light reflected on the reflective surfaces of the polygon mirror 21 is guided to the beam expander 22.

The beam expander 22 is a Keplerian beam expander with a magnification of 1. The beam expander 22 includes a lens 22a, a field lens 22b, and a lens 22c. The laser light reflected on the polygon mirror 21 is incident on the reflective surface of the rotating mirror 23 through the lens 22a, the field lens 22b, and the lens 22c.

The rotating mirror 23 is used for horizontal scanning by reflecting the light scanned by the polygon mirror 21. While the polygon mirror 21 performs high-speed vertical scanning, the rotating mirror 23 performs horizontal scanning at a lower speed than the polygon mirror 21. The rotating mirror 23 is rotatable about a second rotation axis P2. The second rotation axis P2 is arranged perpendicular to the first rotation axis P1. Further, the second rotation axis P2 is arranged substantially in parallel to the optical axis of the two-dimensional scanning optical system 20. The rotating mirror 23 may be, for example, a Dove prism, a double Dove prism or a rotation prism.

The polygon mirror 21 is an example of "first scanner", and the vertical direction is an example of "first direction". Besides, the rotating mirror 23 is an example of "second scanner", and the horizontal direction is an example of "second direction".

Refractive Optical System 30

The refractive optical system 30 deflects the light deflected by the two-dimensional scanning optical system 20 in a second angle range that is wider than the first angle range, and emits the light to the concave mirror 40. The second angle range may be a half-angle of view of 30 degrees or more. That is, the refractive optical system 30 is a wide-angle optical system. Preferably, the second angle range is a half-angle of view of 45 degrees or more. In this case, the refractive optical system 30 is a super wide-angle optical system. The refractive optical system 30 is arranged such that its exit-side optical axis K substantially coincides with the rotational symmetry axis C (described later) of the concave mirror 40.

The refractive optical system 30 includes meniscus lenses 31 and 32 each having a convex surface that faces the object side (the concave mirror 40 side in FIG. 2), a reflective mirror 33, a meniscus lens 34 having a convex surface that faces the image side (the two-dimensional scanning optical system 20 side in FIG. 2), and a lens drive mechanism 35. In the refractive optical system 30, the meniscus lens 31, the meniscus lens 32, the reflective mirror 33, and the meniscus lens 34 are arranged in this order from the object side to the image side on the optical axis.

The meniscus lenses 31 and 32 form a concave lens group. On the other hand, the meniscus lens 34 forms a convex lens group.

The meniscus lens 31 has a negative refractive power. Among the optical elements that constitute the refractive optical system 30, the meniscus lens 31 is arranged in a position optically closest to the concave mirror 40. Since the meniscus lenses 31 and 32 having a negative refractive power are arranged in this order from the object side to the image side, the optical power of negative lenses are divided to them, and the refractive optical system 30 can achieve better optical characteristics as a wide-angle optical system.

The meniscus lens 34 has a positive refractive power. Among the optical elements that constitute the refractive optical system 30, the meniscus lens 34 is arranged in a position optically closest to the two-dimensional scanning optical system 20. Laser light two-dimensionally scanned by the two-dimensional scanning optical system 20 is incident on the convex surface of the meniscus lens 34.

The reflective surface of the reflective mirror 33 is located at the intersection of the optical axis of the meniscus lens 31 and that of the meniscus lens 34. With this, even when the refractive optical system 30 forms a wide-angle optical system, it can be made shorter in the direction of its optical axis. Thus, the ophthalmologic apparatus 1 with the refractive optical system 30 can be downsized.

The lens drive mechanism 35 moves the meniscus lens 34 in the optical axis direction (directions indicated by arrow f in FIG. 2) of the refractive optical system 30. In other words, the meniscus lens 34 is configured to be movable in the optical axis direction of the refractive optical system 30. The lens drive mechanism 35 includes an actuator that generates drive force to move the meniscus lens 34. Upon receipt of a control signal from a controller 200 (described later), the actuator generates drive force according to the control signal. The drive force is transmitted to the meniscus lens 34 via a drive force transmitting mechanism (not illustrated) to move the meniscus lens 34 to a position indicated by the control signal, thereby implementing the focusing function. This enables diopter scale correction. Incidentally, instead of moving the meniscus lens 34, any one of the collimate lens 11b, the biconvex lenses 12a and 12b may be moved integrally with the condenser lens 14a to implement the focusing function. The focusing function can also be implemented by moving any one of lenses that constitute the beam expander 22. Further, the focusing function can be implemented by a diopter scale adjustment lens arranged between the beam splitter 13 and the polygon mirror 21.

Concave Mirror 40

The concave mirror 40 has a reflective surface in at least part of the rotational symmetry surface, and reflects light emitted from the refractive optical system 30. For example, the rotational symmetry surface may be obtained by rotating a predetermined straight or curved line about the rotational symmetry axis C. The concave mirror 40 is arranged such that the rotational symmetry axis C of the rotational symmetry surface thereof substantially coincides with the exit-side optical axis K of the refractive optical system 30. The pupil location (entrance or exit pupil location) in the refractive optical system 30 and the exit focus of the concave mirror 40 (F2 in FIG. 2) are located at optically conjugate positions or around the positions. The exit focus is located at the subject's eye position where the subject's eye E (specifically, the pupil in the center of the iris Ei of the subject's eye E) is located.

In this embodiment, the concave mirror 40 is described as an ellipsoidal mirror. The concave mirror 40 has a first focus F1 and a second focus F2. The first focus F1 is located at the exit pupil location in the refractive optical system 30 or in the vicinity of the exit pupil location. The second focus F2 is located at the subject's eye position. Accordingly, the concave mirror 40 guides light emitted from the refractive optical system 30 to the subject's eye position.

The aperture stop 11c, the reflective surface of the polygon mirror 21, the reflective surface of the rotating mirror 23, the first focus F1, and the second focus F2 are located at optically conjugate positions.

At least the refractive optical system 30 is an off-axis optical system. That is, the second angle range is located in a region deviated from the exit-side optical axis K. In the embodiment, the two-dimensional scanning optical system 20 and the refractive optical system 30 use a half of the region with respect to their respective optical axes. With this, regular reflection light from the subject's eye E is not used for image forming. Therefore, ghost images are suppressed from being formed in the front image of the eye fundus Ef, and thus degradation in image quality can be prevented.

In the optical system 100 (the irradiation optical system 10) configured as above, the parallel flux of laser light output from the light source unit 11 is changed by the beam expander 12 to have a predetermined diameter, and then guided to the beam splitter 13. In the laser light output from the light source unit 11, its components (similarly referred to as laser light) that have passed through the beam splitter 13 are guided to the two-dimensional scanning optical system 20.

The two-dimensional scanning optical system 20 two-dimensionally deflects the laser light that have passed through the beam splitter 13. The laser light output from the two-dimensional scanning optical system 20 is two-dimensionally deflected collimated light. The collimated light is deflected by the refractive optical system 30 to the reflective surface of the concave mirror 40. The concave mirror 40 guides the laser light output from the refractive optical system 30 to the second focus F2 where the subject's eye E is positioned.

The laser light having entered the subject's eye E is scattered in the anterior segment of the subject's eye E. Besides, part of the laser light having entered the subject's eye E passes through the pupil in the center of the iris Ei and the crystal lens Ec, and then is focused on the eye fundus Ef as a spot light. For example, when an eye fundus conjugate surface Pc that can be changed by the meniscus lens 34, which is configured to be movable in the optical axis direction of the refractive optical system 30, is located in a position optically conjugate to the eye fundus Ef, the laser light forms a clear spot light on the eye fundus Ef.

The return light (sometimes referred to as "eye fundus return light) of laser light that has illuminated the eye fundus Ef is the light that returns from the position where the spot light is formed (or in the vicinity of the position) to the ophthalmologic apparatus 1. The eye fundus return light includes scattered laser light (reflected light, backward scattered light, etc.) in the eye fundus Ef, fluorescence that uses the laser light as excitation light, its scattered light, and the like. The eye fundus return light passes through the crystal lens Ec and the pupil, and is emitted from the subject's eye E.

On the other hand, part of the laser light having entered the subject's eye E is scattered in the anterior segment of the subject's eye E. The scattered light (anterior eye scattered light) includes cornea reflected light and the like. At least part of the anterior eye scattered light returns to the ophthalmologic apparatus 1 together with the eye fundus return light (sometimes referred to as "anterior eye return light"). Hereinafter, the eye fundus return light and the anterior eye return light are sometimes collectively referred to as "return light".

The return light from the subject's eye E travels through the concave mirror 40, the refractive optical system 30, and the two-dimensional scanning optical system 20 in this order, and is guided to the beam splitter 13. Components of the return light that have been reflected by the beam splitter 13 are guided to the light receiver 14.

The return light guided to the light receiver 14 is converged by the condenser lens 14a into a focused light, and is guided to the confocal pinhole 14b. The return light that has passed through the confocal pinhole 14b is detected by the light receiving element 14c. The light receiving element 14c photoelectrically converts the return light, and outputs an electrical signal (light-receiving signal).

The above process corresponds to the measurement of a point of the eye fundus Ef, and also corresponds to the measurement in a region of the eye fundus Ef irradiated with a single spot light. In this embodiment, two-dimensional deflection by the two-dimensional scanning optical system 20 moves the region of the eye fundus Ef irradiated with a spot light.

Figure 3:
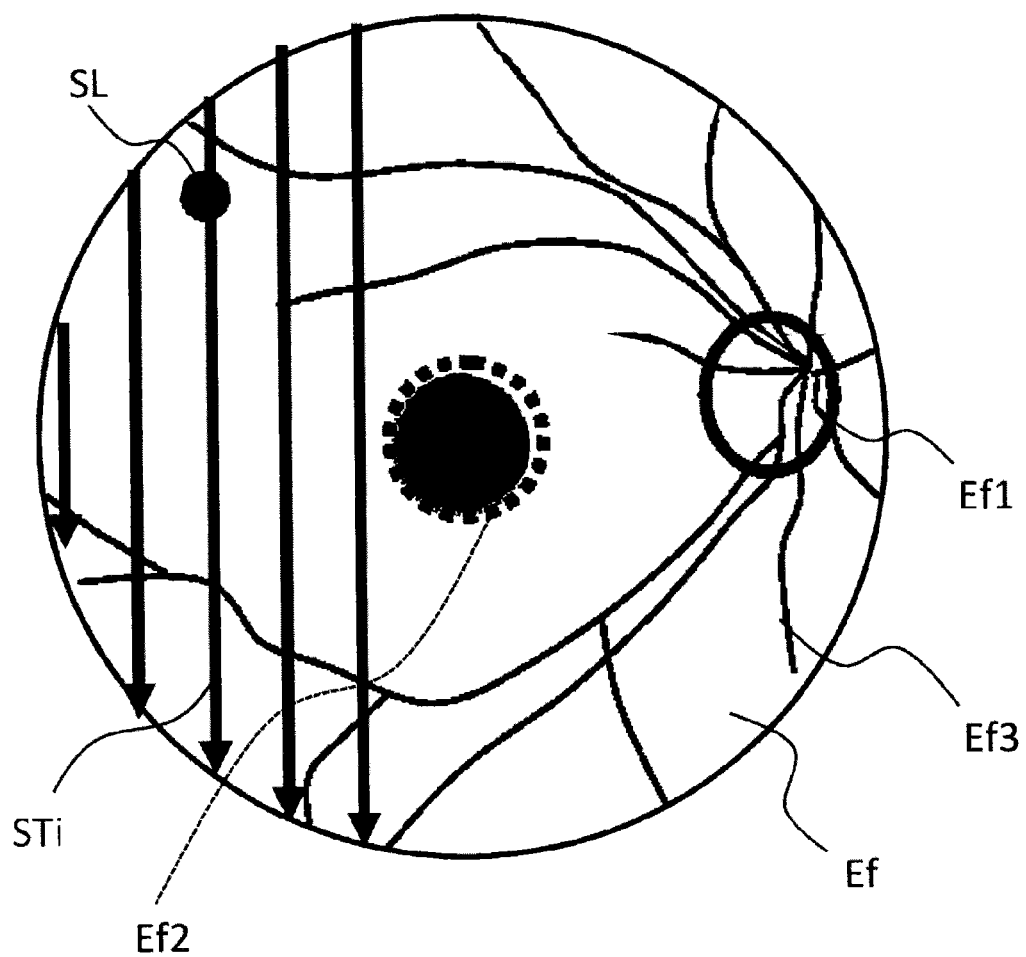
FIG. 3 is a schematic diagram illustrating an example of scanning by the ophthalmologic apparatus of the first embodiment.

FIG. 3 is a schematic diagram for explaining the region irradiated with a spot light in the embodiment. In FIG. 3, a region SL is irradiated with a spot light in the eye fundus Ef. FIG. 3 illustrates an optic disk Ef1, a macula Ef2, and blood vessels Ef3. In FIG. 3, like parts are designated by like reference numerals as in FIG. 1 and repetitious description of such parts may not be provided.

As a result of the two-dimensional deflection of laser light by the two-dimensional scanning optical system 20, the region (irradiated region) SL irradiated with a spot light moves. For example, the irradiated region SL moves along a plurality of parallel straight tracks ST1 to STN ($1 \leq i \leq N$, i and N are integers) running in the same direction. Note that movement patterns of the irradiated region SL are not limited to this. For other examples, the irradiated region SL may move along a plurality of parallel straight tracks running alternately in opposite directions, non-parallel straight tracks, curved tracks, or the like. The light receiving element 14c detects return light from each irradiated region SL and outputs a light-receiving signal. Triggered by this, measurements are sequentially performed in a plurality of positions of the eye fundus Ef.

As described above, the laser light that has been two-dimensionally deflected by the two-dimensional scanning optical system 20 can be emitted by the refractive optical system 30 in wide angles toward the reflective surface of the concave mirror 40. Thus, in the second focus F2, the laser light can be emitted to the subject's eye position in a range of ($2\times\theta$) degrees. For example, $\theta$ is 65 degrees. Accordingly, the eye fundus Ef can be observed in a wide view with a compact apparatus having one concave mirror. Besides, the use of the refractive optical system 30 in addition to the reflective optical system enables aberration correction that is difficult by only the reflective optical system, thereby further improving image quality. In this embodiment, the optical axis of the refractive optical system 30 is bent by the reflective mirror 33. This offers greater flexibility to arrange the optical elements and the drive mechanism, thus enabling further downsizing of the apparatus.

In the above configuration, although the light source unit 11 is described as outputting one type of laser light for the sake of simplicity, it may be configured to output a plurality of types of light. For example, the light source unit 11 may include a plurality of light sources with different output wavelengths, a collimate lens corresponding to each of the light sources, and an optical member (a dichroic mirror, etc.) that combines the optical paths. Further, the light receiver 14 may also be provide with an optical member (a dichroic mirror, etc.) that splits the optical path from the beam splitter 13 into a plurality of paths, in each of which a condenser lens and a light receiver are arranged.

The laser light output from the light source 11a may have arbitrary wavelength. For example, the light source 11a may output infrared laser light, visible laser light, or the like. Further, the light source 11a may selectively output laser lights of different wavelengths. For example, the light source 11a may selectively output infrared laser light and visible laser light.

Processing System

As illustrated in FIG. 1, the processing system includes a calculator, a controller, a storage device such as a random access memory (RAM), a read-only memory (ROM), and a hard disk drive (HDD), a user interface, a communication interface, and the like. In this embodiment, the processing system includes the controller 200, a power supply 210, a light source controller 220, the image forming unit 230, a data processor 240, and a user interface (UI) 250. The processing system is configured centering on the controller 200.

Controller 200

The controller 200 controls each unit of the apparatus. The controller 200 includes a microprocessor and a storage device. The storage device stores in advance computer programs for controlling the ophthalmologic apparatus 1. The computer programs include a light source control program, a two-dimensional scanning optical system control program, a power supply control program, an integrated control program, and the like. The microprocessor operates under these computer programs, and thereby the controller 200 performs the control operation.

Examples of the control operation for the optical system include control of the light source 11a via the light source controller 220, control of the two-dimensional scanning optical system 20, and control of the movement of the meniscus lens 34. Examples of the control operation for the processing system include control of the operation of each unit.

During optical measurement of the eye fundus Ef or after the completion of the optical measurement, the controller 200 generates a pixel location signal and sends it to the image forming unit 230. The pixel location signal indicates the location of a plurality of pixels corresponding to the location of regions SL irradiated with a plurality of spot lights (i.e., the light deflection pattern of the two-dimensional scanning optical system 20) according to the two-dimensional scanning optical system control program.

Power Supply 210

The power supply 210 supplies electrical power received from a commercial power supply, non-utility generation facilities, a battery, or the like to each unit of the ophthalmologic apparatus 1. By controlling the power supply 210, the controller 200 switches power supply modes. Examples of the power supply modes include normal mode, power saving mode, and sleeping mode.

Light Source Controller 220

The light source controller 220 controls the light source 11a under the control of the controller 200. The light source controller 220 controls the light source 11a, for example, by controlling power supplied from the power supply 210. When there is a plurality of light sources, the light source controller 220 selectively supplies power to the light sources under the control of the controller 200. With this, the light sources are selectively used. The light source controller 220 includes, for example, a microprocessor and a storage device. The light source controller 220 may also include a dedicated hardware.

Image Forming Unit 230

The image forming unit 230 generates image data based on a light-receiving signal fed from the light receiver 14 and a pixel location signal fed from the controller 200. The image data corresponds to the front image of the eye fundus Ef.

The image forming unit 230 includes, for example, a microprocessor and a storage device. The storage device stores in advance an image forming program. The microprocessor operates under the image forming program, and thereby at least part of the image forming process is performed. The image forming unit 230 may further include a dedicated hardware.

The image forming unit 230 includes an analog-to-digital (A/D) converter 231, a fundus image generator 232, and a memory 233.

The A/D converter 231 converts the light-receiving signal (analog signal) fed from the light receiver 14 to a digital signal.

The fundus image generator 232 generates image data corresponding to the front image of the eye fundus Ef based on the digital signal fed from the A/D converter 231 and a pixel location signal fed from the controller 200. The process of generating the image data includes the process of associating information (pixel value of brightness, etc.) based on the digital signal corresponding to each region SL irradiated by a spot light with a pixel location corresponding to the irradiated region SL.

The memory 233 functions as an internal memory of the image forming unit 230, and temporarily stores the image data generated by the fundus image generator 232. Incidentally, the memory 233 is arbitrarily used. The image data generated by the image forming unit 230 is sent to the controller 200.

Data Processor 240

The data processor 240 performs various types of data processing. Examples of the data processing include processing of image data generated by the image forming unit 230 or other devices. This processing includes, for example, various types of image processing and diagnosis support such as image evaluation based on the image data.

The data processor 240 may be part of the ophthalmologic apparatus 1 or an external device. In the former case, the data processor 240 includes, for example, a microprocessor and a storage device. The storage device stores in advance one or more data processing programs. The microprocessor operates under the data processing programs, and thereby data processing is performed. The data processor 240 may also include a dedicated hardware.

In the latter case, the data processor 240 includes a computer. The computer may be, for example, a personal computer, a smart phone, a tablet terminal, a personal digital assistant (PDA), a server, or the like. The controller 200 includes an interface for communication with the computer. When the computer has a display function, the data processor 240 as an external device performs display process based on information sent from the controller 200. Examples to be displayed by this process include images based on image data, capturing date and time information, capturing conditions (scan conditions, type of the light source 11a, amount of capturing light, etc.), and the like. When the computer has a database function, the data processor 240 stores information sent from the controller 200. The processing results obtained by the data processor 240 may be sent to the ophthalmologic apparatus 1 (the controller 200) and other devices.

In both the former and latter cases, the functions of the data processor 240 are not limited as described above.

User Interface 250

The user interface 250 has a display function and an operation/input function. The display function is implemented by a display device such as a liquid crystal display (LCD). The display device displays information under the control of the controller 200.

The operation/input function is implemented by an operation device or an input device. Examples of such devices include a button, a lever, a knob, a mouse, a keyboard, and a trackball. The controller 200 may display a graphical user interface (GUI) on the display device. The display device may have a touch screen.

Configuration Example of Processing System

Figure 4:
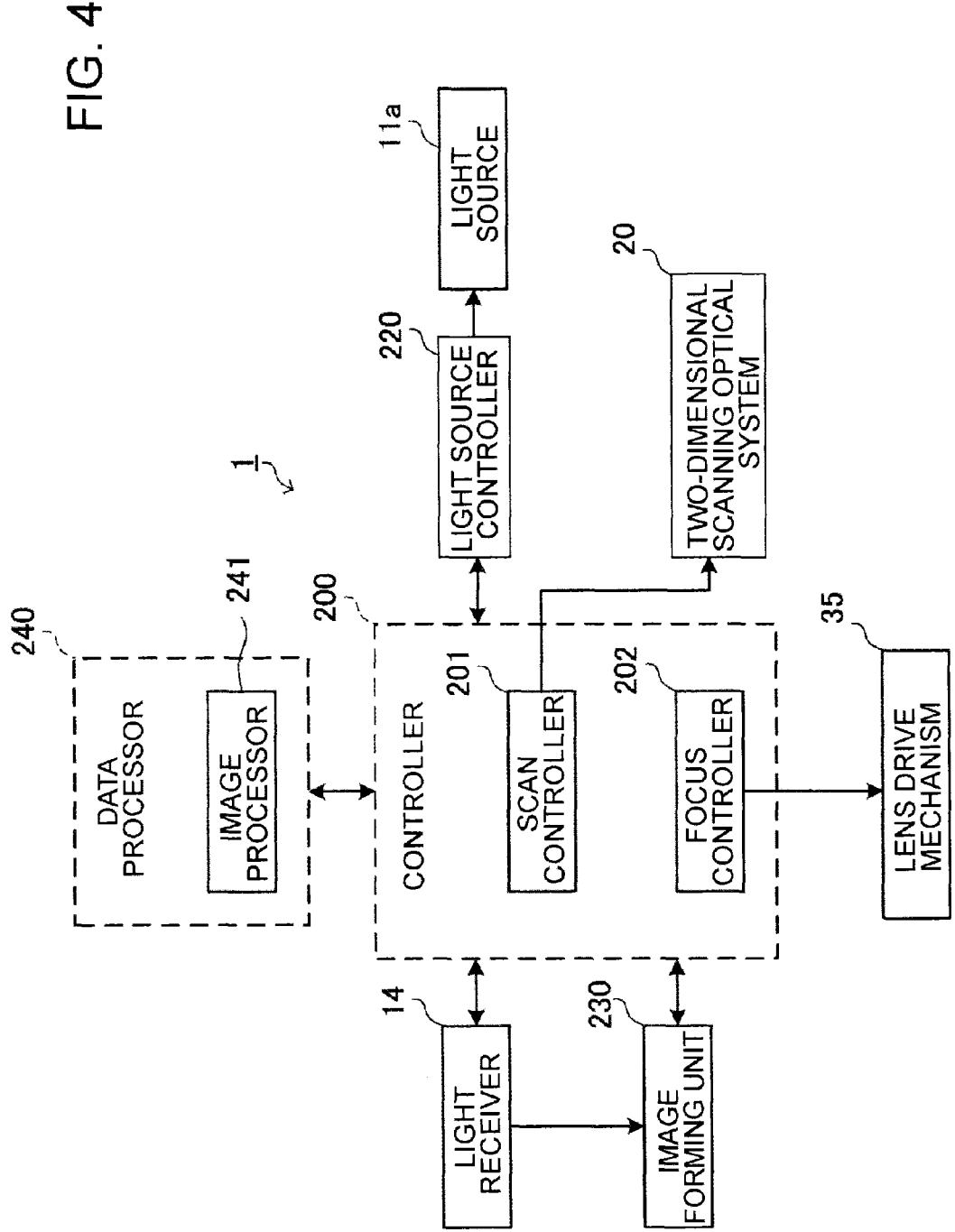
FIG. 4 is a functional block diagram illustrating an example of the configuration of the ophthalmologic apparatus of the first embodiment.

FIG. 4 is a functional block diagram illustrating an example of the configuration of the processing system in the ophthalmologic apparatus 1. FIG. 4 does not illustrate parts not necessary for explaining the operation of this embodiment. In FIG. 4, like parts are designated by like reference numerals as in FIG. 1 or 2 and repetitious description of such parts may not be provided.

The controller 200 performs various types of processes as well as controlling each unit of the apparatus. The controller 200 includes a scan controller 201 and a focus controller 202.

The scan controller 201 controls the two-dimensional scanning optical system 20, and thereby two-dimensionally deflects laser light to perform two-dimensional scanning. Specifically, for example, the scan controller 201 rotates the polygon mirror 21 about the first rotation axis P1, and also rotates the rotating mirror 23 about the second rotation axis P2 along with the rotation of the polygon mirror 21. With this, the scan controller 201 controls the two-dimensional scanning of laser light in the region SL irradiated with a spot of laser light as illustrated in FIG. 3.

The focus controller 202 controls the lens drive mechanism 35, and thereby moves the meniscus lens 34 to a desired position. Specifically, for example, the focus controller 202 moves the meniscus lens 34 to an arbitrary position on the optical axis of the refractive optical system 30 to achieve focusing as instructed by a user via the user interface 250. That is, in response to an instruction of a user input through the user interface 250, the focus controller 202 sends a control signal to an actuator of the lens drive mechanism 35. The actuator of the lens drive mechanism 35 generates a driving force according to the control signal and moves the meniscus lens 34 to an instructed position.

The data processor 240 includes an image processor 241. The image processor 241 performs predetermined image processing on the front image of the eye fundus Ef formed by the image forming unit 230. If the ophthalmologic apparatus 1 has the function of forming another type of image (e.g., anterior eye image, tomographic image obtained by OCT), the image processor 241 can perform predetermined image processing on the image. Further, if the ophthalmologic apparatus 1 has the function of receiving an image captured by another device, the image processor 241 can perform predetermined image processing on the image.

Operation Example

Described below is an example of the operation of the ophthalmologic apparatus 1.

When a user instructs desired focusing using the user interface 250, the focus controller 202 sends a control signal corresponding to the instruction to the lens drive mechanism 35. In response to the control signal, the lens drive mechanism 35 moves the meniscus lens 34 to an instructed position.

Subsequently, upon receipt of a predetermined trigger such as an instruction to start scanning from the user via the user interface 250, the controller 200 controls the light source controller 220 so that the light source unit 11 outputs laser light. The controller 200 also controls the two-dimensional scanning optical system 20 through the scan controller 220 to scan the eye fundus Ef with the laser light output from the light source unit 11.

When the eye fundus Ef is irradiated with the laser light, the light receiver 14 (the light receiving element 14c) receives return light thereof as described above. The light receiving element 14c sends a light-receiving signal to the image forming unit 230.

The image forming unit 230 forms a front image of the eye fundus Ef based on the light-receiving signal. The controller 200 may display the front image formed by the image forming unit 230 on the display device of the user interface 250.

The controller 200 sends the front image to the image processor 241. The image processor 241 forms a processed image based on the front image fed from the controller 200. The processed image is sent to the controller 200. The controller 200 displays the front image formed by the image forming unit 230 and the processed image formed by the image processor 241 on the display device of the user interface 250 in arbitrary display mode. For example, the controller 200 may selectively display front images specified by a user. Besides, the controller 200 may display a processed image together with a front image used for forming the processed image.

Action and Effects

Action and effects of the ophthalmologic apparatus 1 of this embodiment is described.

The ophthalmologic apparatus 1 includes the two-dimensional scanning optical system 20, the refractive optical system 30, and the concave mirror 40. The two-dimensional scanning optical system 20 deflects light form the light source 11 a in the first angle range. The refractive optical system 30 deflects the light deflected by the two-dimensional scanning optical system 20 in the second angle range that is wider than the first angle range. The concave mirror 40 has a reflective surface in at least part of the rotational symmetry surface, and reflects the light emitted from the refractive optical system 30. The refractive optical system 30 is arranged such that its exit-side optical axis K substantially coincides with the rotational symmetry axis C of the rotational symmetry surface. The pupil location (entrance or exit pupil location) in the refractive optical system 30 and the exit focus of the concave mirror 40 (the second focus F2) are located at optically conjugate positions or in the vicinity of the positions. The exit focus (second focus F2) is located at the subject's eye position.

With the ophthalmologic apparatus 1 as described above, the laser light that has been two-dimensionally deflected by the two-dimensional scanning optical system 20 can be emitted from the refractive optical system 30 in wide angles toward the reflective surface of the concave mirror 40. Thus, in the exit focus of the concave mirror 40 (the second focus F2), the laser light can be emitted to the subject's eye E in a range of (2×θ) degrees. Accordingly, the eye fundus Ef can be observed in a wide view with a compact apparatus having one concave mirror. Besides, the use of the refractive optical system 30 in addition to the reflective optical system enables aberration correction and the like, thereby further improving image quality.

The ophthalmologic apparatus 1 may include the light receiver 14. The light receiver 14 receives return light traveling back from the subject's eye position through the concave mirror 40, the refractive optical system 30, and the two-dimensional scanning optical system 20 in this order. The two-dimensional scanning optical system 20 may include the polygon mirror 21 (the first scanner) and the rotating mirror 23 (the second scanner). The polygon mirror 21 is arranged to be rotatable about the first rotation axis P1, and is used for scanning in the vertical direction (first direction) by reflecting light form the light source 11a. The rotating mirror 23 is arranged to be rotatable about the second rotation axis P2 that is perpendicular to the first rotation axis P1, and is used for scanning in the horizontal direction (second direction) by reflecting the light scanned by the polygon mirror 21. The reflective surface of the polygon mirror 21 and that of the rotating mirror 23 are located at optically conjugate positions.

Further, the second rotation axis P2 of the rotating mirror 23 may be arranged substantially in parallel to the optical axis of the two-dimensional scanning optical system 20. This prevents degradation in image quality due to the return light in the two-dimensional scanning optical system 20.

The refractive optical system 30 may include the meniscus lens 31 (first optical element) and the meniscus lens 34 (second optical element). The meniscus lens 31 is arranged in a position optically closest to the concave mirror 40. The meniscus lens 34 is arranged in a position optically closest to the two-dimensional scanning optical system 20. The meniscus lens 34 is configured to be movable in the optical axis direction of the refractive optical system 30. This enables diopter scale correction.

The refractive optical system 30 may further include the reflective mirror 33 (reflection unit). The reflective mirror 33 is arranged such that its reflective surface is located at the intersection of the optical axis of the meniscus lens 31 and that of the meniscus lens 34. In this embodiment, the optical axis of the refractive optical system 30 is bent by the reflective mirror 33. This offers greater flexibility to arrange the optical elements and the drive mechanism, thus enabling further downsizing of the ophthalmologic apparatus 1.

Second Embodiment

In the first embodiment, an example is described in which the two-dimensional scanning optical system 20 horizontally deflects laser light output form the light source 11a by the rotating mirror 23 while vertically deflecting the light by the polygon mirror 21. However, this is by way of example and not by way of limitation. In a second embodiment, an example is described in which the two-dimensional scanning optical system vertically deflects laser light output form the light source by the polygon mirror while horizontally deflecting the light by the rotating mirror.

The ophthalmologic apparatus of the second embodiment is basically similar to that of the first embodiment. Therefore, the ophthalmologic apparatus of the second embodiment is described below mainly about the differences from the first embodiment.

Figure 5:
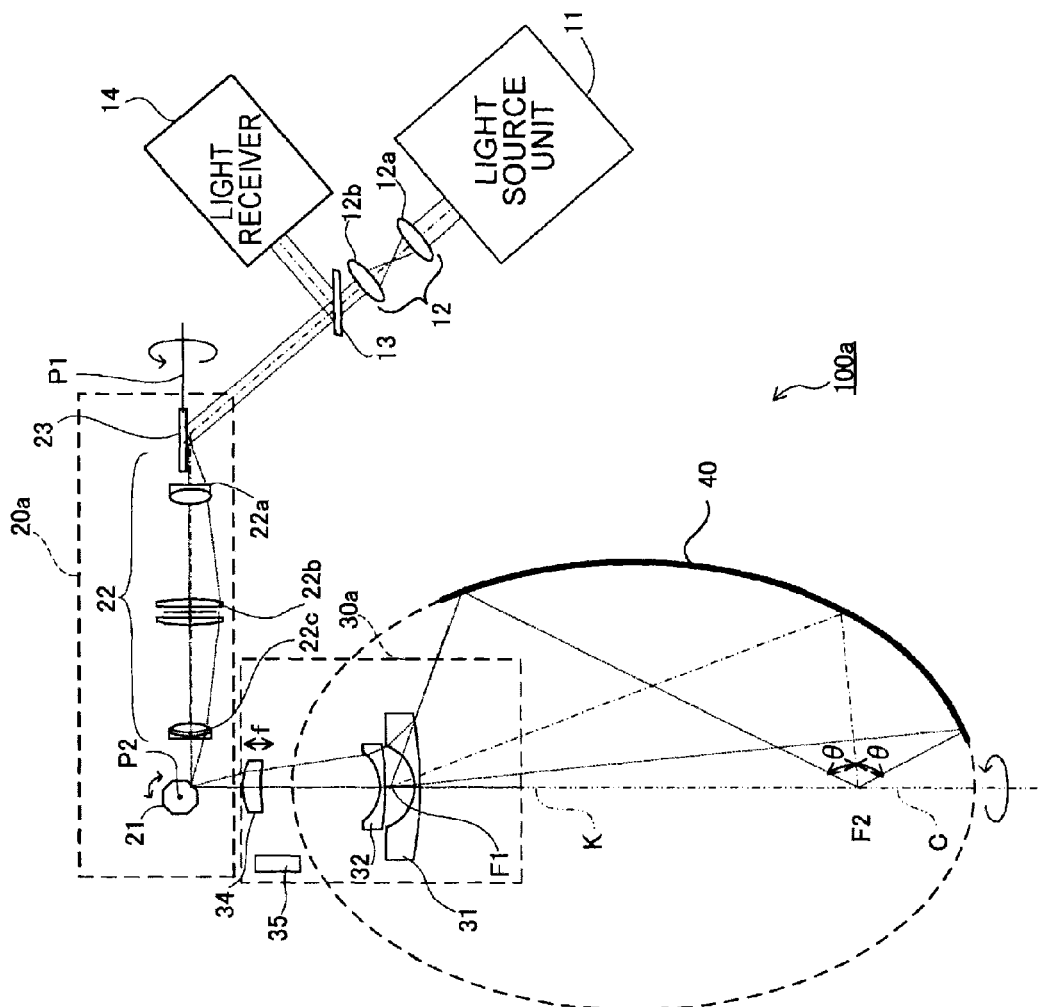
FIG. 5 is a schematic diagram illustrating an example of the configuration of an optical system according to a second embodiment.

FIG. 5 is a schematic diagram illustrating an example of the configuration of an optical system according to the second embodiment. In FIG. 5, like parts are designated by like reference numerals as in FIG. 2 and repetitious description of such parts may not be provided.

An optical system 100a of the second embodiment includes an irradiation optical system as in the first embodiment. The optical system 100a of the second embodiment is different from the optical system 100 of the first embodiment in having a two-dimensional scanning optical system 20a and a refractive optical system 30a in place of the two-dimensional scanning optical system 20 and the refractive optical system 30, respectively.

The two-dimensional scanning optical system 20a includes the polygon mirror 21, the beam expander 22, and the rotating mirror 23.

The rotating mirror 23 is used for horizontal scanning by reflecting laser light output form the light source unit 11. The rotating mirror 23 is rotatable about the first rotation axis P1. The first rotation axis P1 is arranged substantially in parallel to the optical axis of the two-dimensional scanning optical system 20a. The reflective surface of the rotating mirror 23 is irradiated with laser light output form the light source unit 11. The laser light reflected form the rotating mirror 23 is guided to the beam expander 22.

The polygon mirror 21 is used for vertical scanning by reflecting the light scanned by the rotating mirror 23. The polygon mirror 21 has a plurality of reflective surfaces each arranged substantially in parallel to the second rotation axis P2, and is rotatable about the second rotation axis P2. The second rotation axis P2 is arranged perpendicular to the first rotation axis P1.

In this embodiment, the rotating mirror 23 is an example of "first scanner", and the polygon mirror 21 is an example of "second scanner".

The refractive optical system 30a deflects light deflected by the two-dimensional scanning optical system 20a in the second angle range that is wider than the first angle range, and emits the light to the concave mirror 40. The second angle range may be a half-angle of view of 30 degrees or more. That is, the refractive optical system 30a is a wide-angle optical system. Preferably, the second angle range is a half-angle of view of 45 degrees or more. In this case, the refractive optical system 30a is a super wide-angle optical system. The refractive optical system 30a is arranged such that its exit-side optical axis K substantially coincides with the rotational symmetry axis C of the concave mirror 40.

The refractive optical system 30a includes the meniscus lenses 31 and 32 each having a convex surface that faces the object side, the meniscus lens 34 having a convex surface that faces the image side, and the lens drive mechanism 35. That is, the refractive optical system 30a has the configuration of the refractive optical system 30 without the reflective mirror 33.

The ophthalmologic apparatus of the second embodiment may be configured with the use of the optical system 100a instead of the optical system 100 of the first embodiment. The ophthalmologic apparatus provided with the optical system 100a operates in the same manner as in the first embodiment. Accordingly, the ophthalmologic apparatus provided with the optical system 100a as illustrated in FIG. 5 can achieve the same effects as in the first embodiment.

Incidentally, in the first and the second embodiments, the polygon mirror 21 may be used for horizontal scanning, and the rotating mirror 23 may be used for vertical scanning.

Action and Effects

Action and effects of the ophthalmologic apparatus of this embodiment are described.

The ophthalmologic apparatus of this embodiment includes the two-dimensional scanning optical system 20a, the refractive optical system 30a, and the concave mirror 40. The two-dimensional scanning optical system 20a includes the rotating mirror 23 (the first scanner) and the polygon mirror 21 (the second scanner). The rotating mirror 23 is arranged to be rotatable about the first rotation axis P1, and is used for scanning in the horizontal direction by reflecting light form the light source 11a. The polygon mirror 21 is arranged to be rotatable about the second rotation axis P2, and is used for scanning in the vertical direction by reflecting the light scanned by the rotating mirror 23. In this manner, the rotating mirror may be used as a scanner for scanning in a predetermined direction by reflecting light form the light source 11a. In this case also, the rotation axis of the rotating mirror is arranged substantially in parallel to the optical axis of the two-dimensional scanning optical system.

With the ophthalmologic apparatus as described above, the laser light that has been scanned by the two-dimensional scanning optical system 20a can be emitted from the refractive optical system 30a in wide angles toward the reflective surface of the concave mirror 40. Thus, in the exit focus of the concave mirror 40 (the second focus F2), the laser light can be emitted to the subject's eye E in a range of (2×θ) degrees. Accordingly, the eye fundus Ef can be observed in a wide view with a compact apparatus having one concave mirror. Besides, the use of the refractive optical system 30a in addition to the reflective optical system enables aberration correction and the like, thereby further improving image quality.

Third Embodiment

In the first and the second embodiments, an example is described in which the optical system includes only the irradiation optical system for observing the front image of the eye fundus Ef. In a third embodiment, an example is described in which the optical system further includes a fixation optical system.

The ophthalmologic apparatus of the third embodiment is basically similar to that of the first embodiment. Therefore, the ophthalmologic apparatus of the third embodiment is described below mainly about the differences from the first embodiment.

Figure 6:
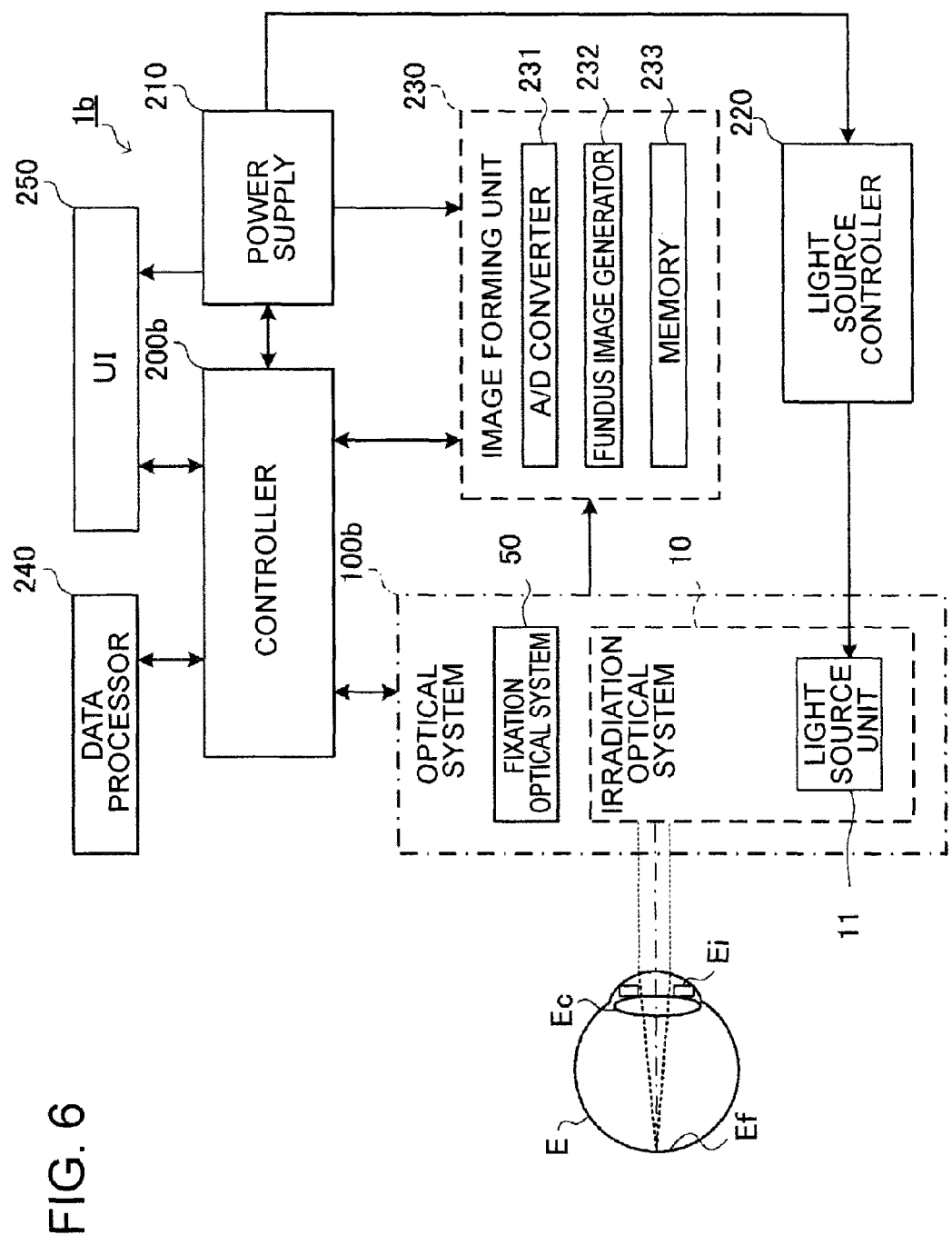
FIG. 6 is a functional block diagram illustrating an example of the configuration of an ophthalmologic apparatus according to a third embodiment.

FIG. 6 is a functional block diagram illustrating an example of the configuration of an ophthalmologic apparatus according to the third embodiment. In FIG. 6, like parts are designated by like reference numerals as in FIG. 1 and repetitious description of such parts may not be provided.

Figure 7:
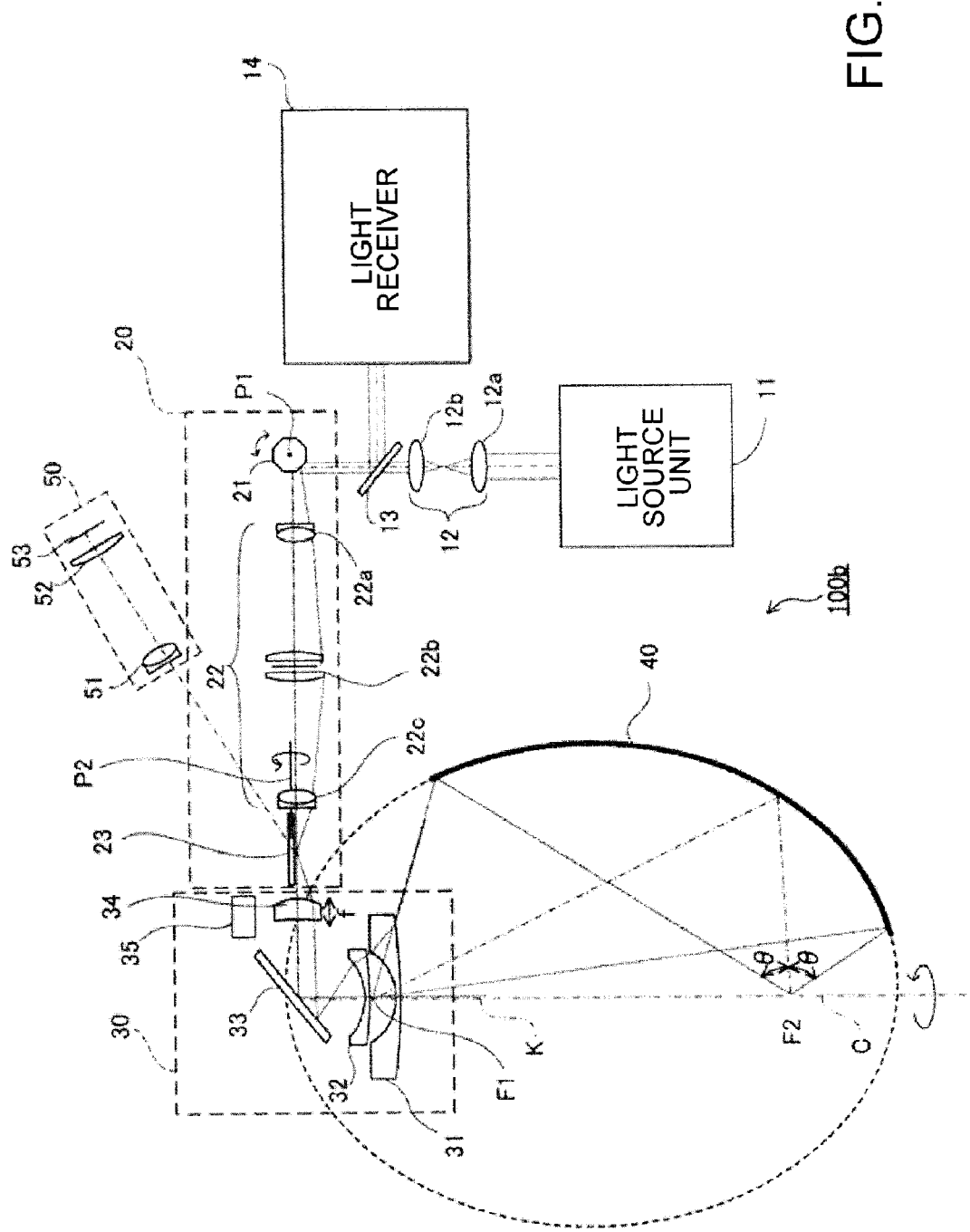
FIG. 7 is a schematic diagram illustrating an example of the configuration of an optical system of the third embodiment.

FIG. 7 is a schematic diagram illustrating an example of the configuration of an optical system illustrated in FIG. 6.

In FIG. 7, like parts are designated by like reference numerals as in FIG. 2 and repetitious description of such parts may not be provided.

An ophthalmologic apparatus 1b of the third embodiment is different from the ophthalmologic apparatus 1 of the first embodiment in having an optical system 100b and a controller 200b in place of the optical system 100 and the controller 200, respectively. The optical system 100b includes the irradiation optical system 10 and a fixation optical system 50.

The fixation optical system 50 is an optical system for projecting a fixation target on the subject's eye E. As illustrated in FIG. 7, the fixation optical system 50 includes a lens 51, a plano-convex lens 52, and an LCD 53. The LCD 53 displays a fixation target under the control of the controller 200b. The fixation target is used to fixate the subject's eye E.

While scanning is not performed by the two-dimensional scanning optical system 20, the fixation optical system 50 projects the fixation target on the subject's eye E. For this reason, when scanning is not performed, the rotating mirror 23 is stopped at a predetermined rotation stop position for projecting the fixation target under the control of the scan controller 201 of the controller 200b. The fixation optical system 50 causes light for projecting the fixation target to enter the reflective surface of the rotating mirror 23 stopped at the rotation stop position. The fixation optical system 50 is arranged such that the light (light for projecting the fixation target) reflected on the reflective surface of the rotating mirror 23 stopped at the rotation stop position is positioned in the center of the scanning range of the two-dimensional scanning optical system 20 when the fixation target is displayed in a predetermined display position on the LCD 53.

The light output from the LCD 53 travels through the plano-convex lens 52 and the lens 51, and reflected on the reflective surface of the rotating mirror 23 stopped at the rotation stop position. Then, the light is reflected on the reflective mirror 33 and deflected by the meniscus lenses 32 and 31, and thereby projected on the subject's eye E.

The controller 200b displays a predetermined fixation target on the LCD 53 in an on-screen display position corresponding to an instruction entered by a user using the user interface 250, for example. By changing the display position of the fixation target on the screen of the LCD 53, the fixation position of the subject's eye E can be changed. Examples of the fixation position of the subject's eye E include a position for acquiring an image centered at a macula of the eye fundus Ef, a position for acquiring an image centered at the optic disc, and a position for acquiring an image centered at the eye fundus center between the macula and the optic disc. The display position of the fixation target can be changed arbitrarily.

Action and Effects

Action and effects of the ophthalmologic apparatus of this embodiment are described.

The ophthalmologic apparatus 1b includes the two-dimensional scanning optical system 20, the refractive optical system 30, and the concave mirror 40. The ophthalmologic apparatus may further include the fixation optical system 50 (first optical system). The fixation optical system 50 is an optical system for projecting a fixation target on the subject's eye E. With the ophthalmologic apparatus 1b, the front image of the eye fundus Ef can be obtained in a wide view with a compact apparatus having one concave mirror while a fixation target is being projected to a desired position on the eye fundus Ef.

Fourth Embodiment

In the third embodiment, an example is described in which a fixation target is projected by the refractive optical system 30 having the reflective mirror 33. However, this is by way of example and not by way of limitation. In a fourth embodiment, an example is described in which the refractive optical system is provided with a half mirror, and a fixation optical system is located in the transmission direction of the half mirror. Incidentally, if the light source unit 11 outputs only infrared laser light, a dichroic mirror may be used instead of the half mirror.

The ophthalmologic apparatus of the fourth embodiment is of basically the same configuration as that of the third embodiment except for the configuration of the optical system. Therefore, the ophthalmologic apparatus of the fourth embodiment is described below mainly about the differences from the third embodiment.

Figure 8:
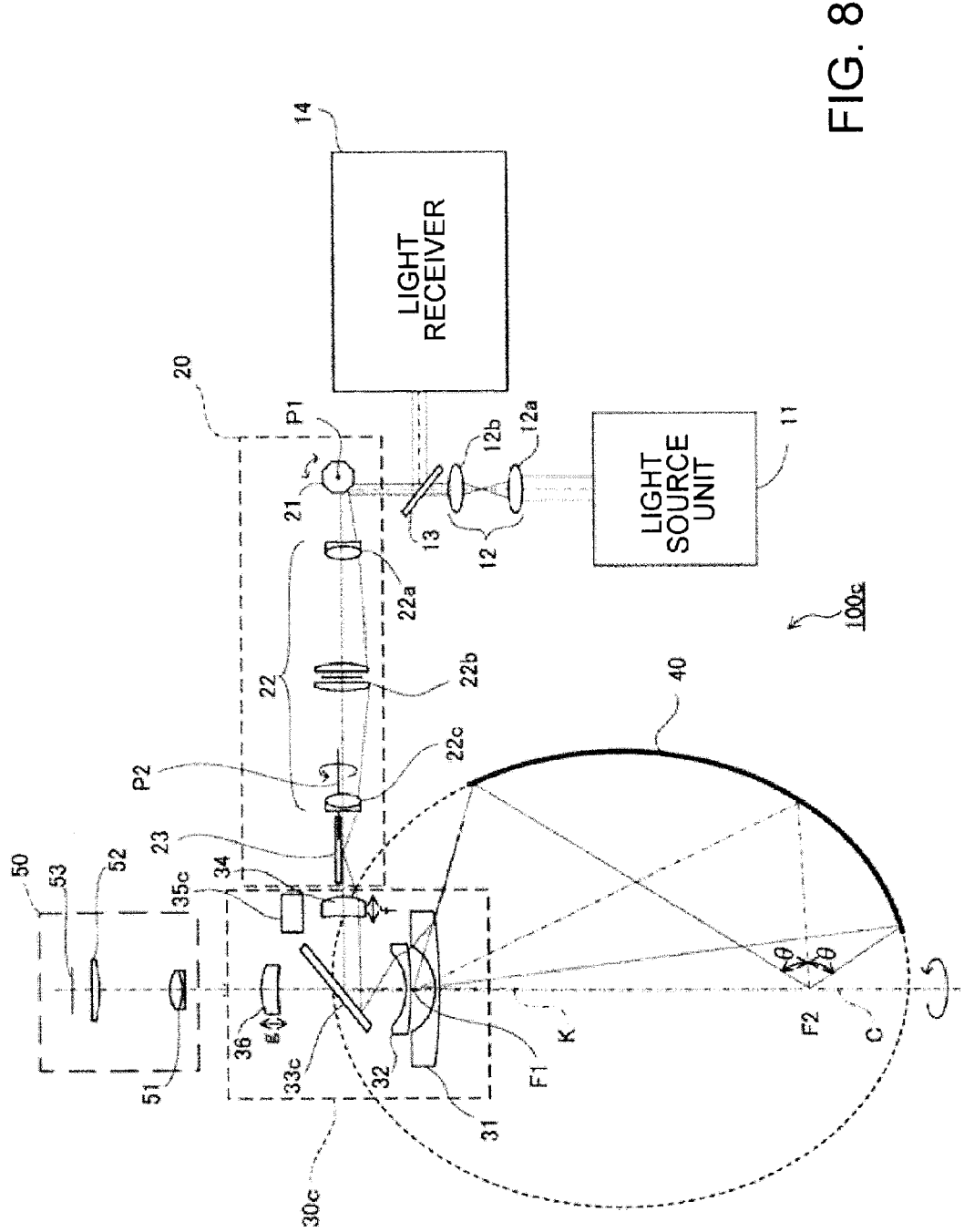
FIG. 8 is a schematic diagram illustrating an example of the configuration of an optical system according to a fourth embodiment.

FIG. 8 is a schematic diagram illustrating an example of the configuration of an optical system according to the fourth embodiment. In FIG. 8, like parts are designated by like reference numerals as in FIG. 7 and repetitious description of such parts may not be provided.

An optical system 100c of the fourth embodiment is different from the optical system 100b of the third embodiment in a refractive optical system 30c and the fixation optical system 50. The refractive optical system 30c is arranged in place of the refractive optical system 30. The fixation optical system 50 is located in the transmission direction of a half mirror of the refractive optical system 30c.

The refractive optical system 30c further deflects light deflected by the two-dimensional scanning optical system 20 in the second angle range that is wider than the first angle range, and emits the light to the concave mirror 40. The second angle range may be a half-angle of view of 30 degrees or more. That is, the refractive optical system 30c is a wide-angle optical system. Preferably, the second angle range is a half-angle of view of 45 degrees or more. In this case, the refractive optical system 30c is a super wide-angle optical system. The refractive optical system 30c is arranged such that its exit-side optical axis K substantially coincides with the rotational symmetry axis C of the concave mirror 40.

The refractive optical system 30c includes the meniscus lenses 31 and 32 each having a convex surface that faces the object side, a half mirror 33c as a beam splitter, the meniscus lenses 34 and 36 each having a convex surface that faces the image side, and a lens drive mechanism 35c.

The half mirror 33c is located between the meniscus lenses 31 and 34 and also between the meniscus lenses 31 and 36. The half mirror 33c combines the optical path of the refractive optical system 30c with that of the fixation optical system 50. Further, the half mirror 33c combines the optical path of the refractive optical system 30c with that of the two-dimensional scanning optical system 20. The reflective surface of the half mirror 33c is located at the intersection of the optical axis of the meniscus lens 31 and that of the meniscus lens 34. The meniscus lens 34 is located in the reflection direction of the half mirror 33c. The meniscus lens 36 is located in the transmission direction of the half mirror 33c. The half mirror 33c is an example of "first beam splitter".

The meniscus lens 36 has a positive refractive power. Among the optical elements that constitute the refractive optical system 30c, the meniscus lens 36 is arranged in a position optically closest to the fixation optical system 50.

Light from the fixation optical system 50 is incident on the convex surface of the meniscus lens 36. Just like the meniscus lens 34, the meniscus lens 36 is configured to be movable in the optical axis direction (directions indicated by arrow g in FIG. 8) in the transmission direction of the half mirror 33c.

The lens drive mechanism 35c moves the meniscus lens 34 in the optical axis direction (directions indicated by arrow f in FIG. 2) in the reflection direction of the half mirror 33c. In addition, the lens drive mechanism 35c moves the meniscus lens 36 in the transmission direction of the half mirror 33c. The lens drive mechanism 35c includes one or more actuators that generate drive force to move the meniscus lenses 34 and 36. Upon receipt of a control signal from the controller (focus controller) of this embodiment, the actuator(s) generates drive force according to the control signal. The drive force is transmitted to either or both the meniscus lenses 34 and 36 via a drive force transmitting mechanism (not illustrated) to move each of them to a position indicated by the control signal. This enables the optical path length to be changeable, thereby implementing the focusing function.

In this embodiment, the light output from the LCD 53 of the fixation optical system 50 travels through the planoconvex lens 52 and the lens 51, and is deflected by the refractive optical system 30c and thereby projected on the eye fundus Ef. The return light from the subject's eye E is reflected in the reflection direction of the half mirror 33c, and received by the light receiver 14 as in the first embodiment.

Action and Effects

Action and Effects of the ophthalmologic apparatus of this embodiment are described.

The ophthalmologic apparatus of the embodiment includes the two-dimensional scanning optical system 20, the refractive optical system 30c, and the concave mirror 40. The refractive optical system 30c deflects light deflected by the two-dimensional scanning optical system 20 in the second angle range that is wider than the first angle range. The concave mirror 40 has a reflective surface in at least part of the rotational symmetry surface, and reflects light emitted from the refractive optical system 30c. The refractive optical system 30c is arranged such that its exit-side optical axis K substantially coincides with the rotational symmetry axis C of the rotational symmetry surface. The pupil location (entrance or exit pupil location) in the refractive optical system 30c and the exit focus of the concave mirror 40 (the second focus F2) are located at optically conjugate positions or in the vicinity of the positions. The exit focus (the second focus F2) is located at the subject's eye position. The ophthalmologic apparatus may further include the first optical system and the half mirror 33c (beam splitter). The first optical system is used to illuminate the subject's eye E with light. The half mirror 33c is located between the meniscus lenses 31 and 34. The half mirror 33c combines the optical path of the refractive optical system 30c with that of the first optical system. The first optical system may include the fixation optical system 50 for projecting a fixation target on the subject's eye E.

With the ophthalmologic apparatus as described above, the front image of the eye fundus Ef can be obtained in a wide view with a compact apparatus having one concave mirror while a fixation target is being projected to a desired position on the eye fundus Ef.

Fifth Embodiment

In the third or the fourth embodiment, an example is described in which the optical system is provided with a fixation optical system in addition to the irradiation optical system. However, this is by way of example and not by way of limitation. In a fifth embodiment, an example is described in which the optical system is provided with a fixation optical system and an optical coherence tomography (OCT) optical system in addition to the irradiation optical system.

The ophthalmologic apparatus of the fifth embodiment is of basically the same configuration as that of the third embodiment except for the configuration of the optical system. Therefore, the ophthalmologic apparatus of the fifth embodiment is described below mainly about the differences from the third embodiment.

Figure 9:
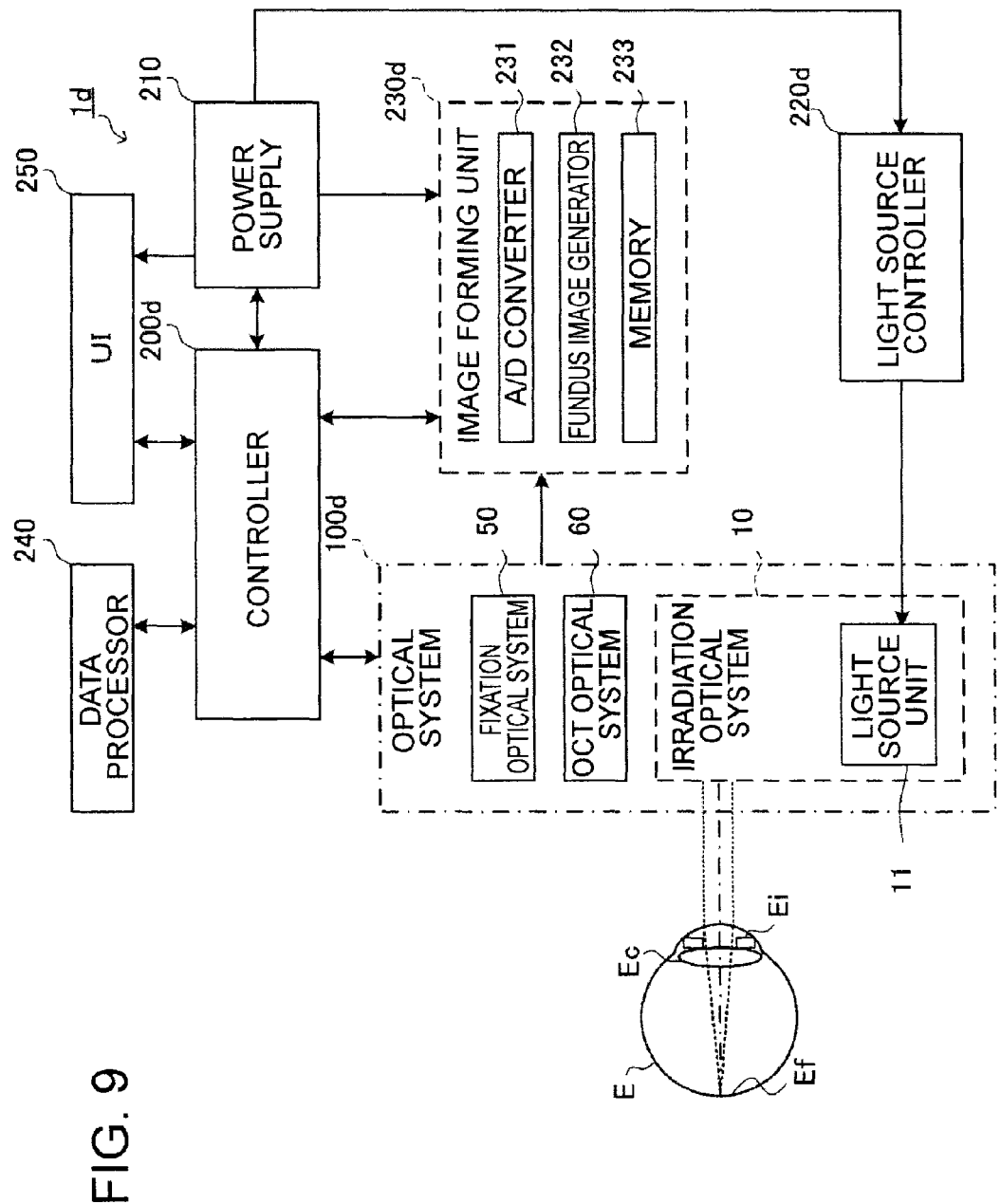
FIG. 9 is a functional block diagram illustrating an example of the configuration of an ophthalmologic apparatus according to a fifth embodiment.

FIG. 9 is a functional block diagram illustrating an example of the configuration of an ophthalmologic apparatus according to the fifth embodiment. In FIG. 9, like parts are designated by like reference numerals as in FIG. 6 and repetitious description of such parts may not be provided.

Figure 10:
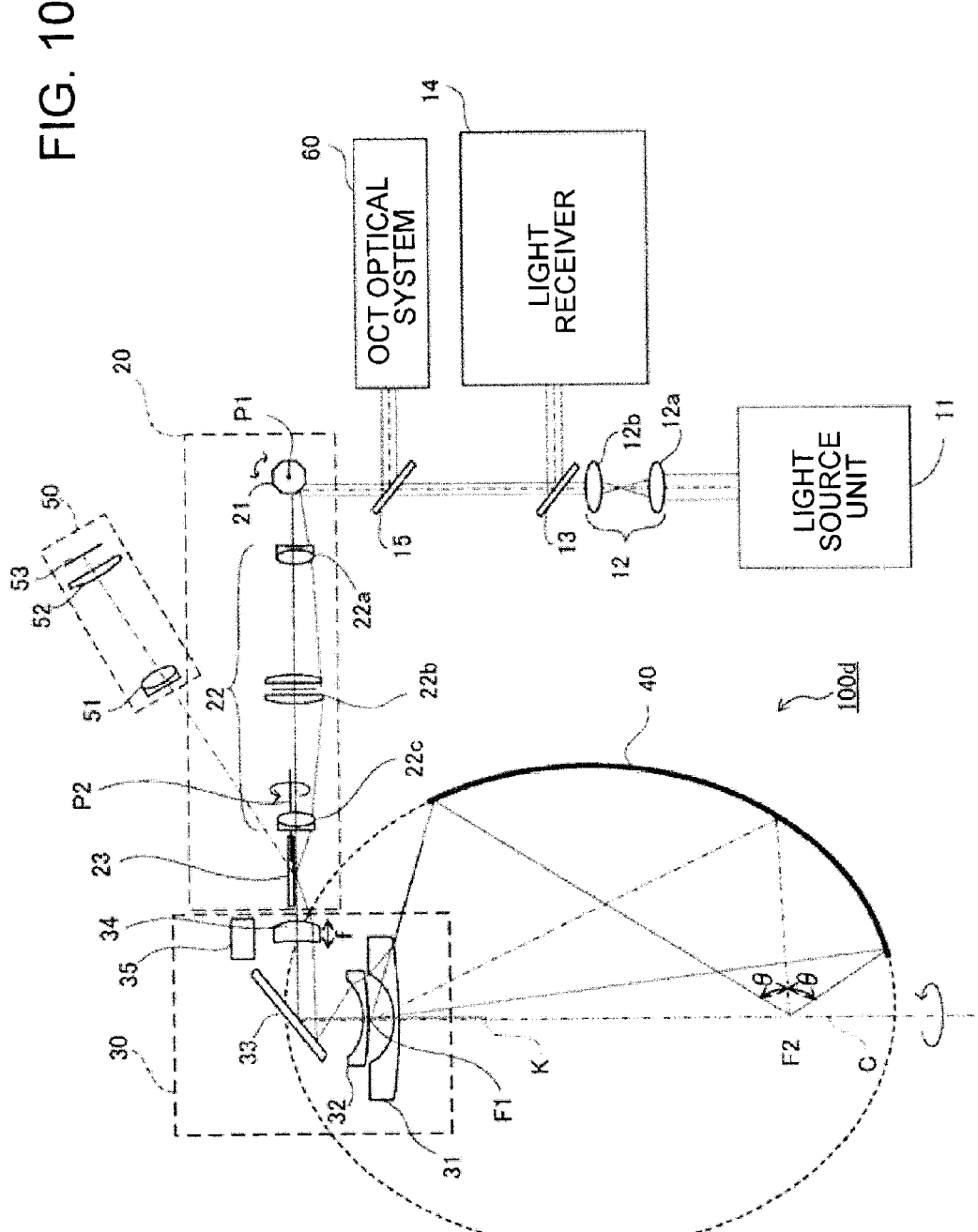
FIG. 10 is a schematic diagram illustrating an example of the configuration of an optical system of the fifth embodiment.

FIG. 10 is a schematic diagram illustrating an example of the configuration of an optical system illustrated in FIG. 9. In FIG. 10, like parts are designated by like reference numerals as in FIG. 7 and repetitious description of such parts may not be provided.

Figure 11:
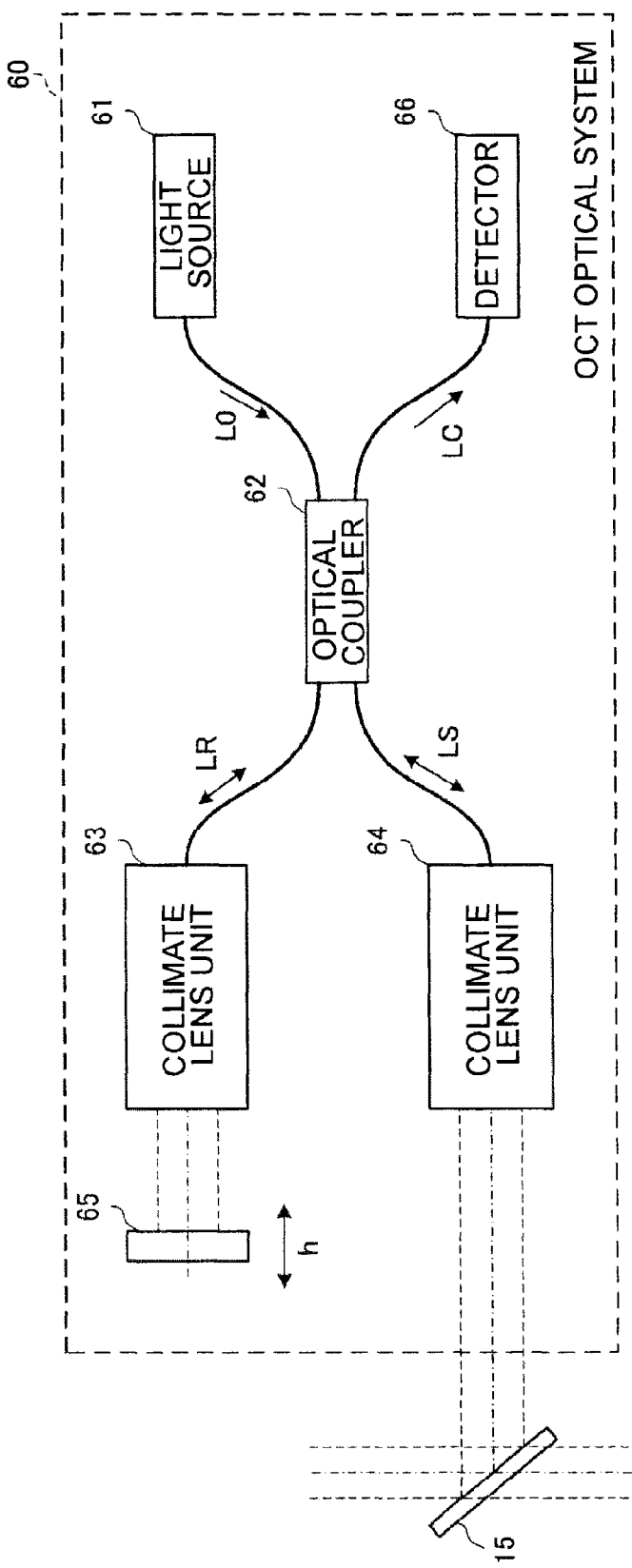
FIG. 11 is a schematic diagram illustrating an example of the configuration of an optical system of the fifth embodiment.

FIG. 11 is a schematic diagram illustrating an example of the configuration of an OCT optical system illustrated in FIG. 10. FIG. 11 also illustrates a beam splitter 15 illustrated in FIG. 10.

An ophthalmologic apparatus 1d of the fifth embodiment is different from the ophthalmologic apparatus 1b of the third embodiment in having an optical system 100d, a controller 200d, a light source controller 220d, and an image forming unit 230d in place of the optical system 100b, the controller 200b, the light source controller 220, and the image forming unit 230, respectively.

The optical system 100d includes the irradiation optical system 10, the fixation optical system 50, and an OCT optical system 60. The OCT optical system 60 is an optical system for acquiring an image of the subject's eye E by OCT. In the optical system 100d, as illustrated in FIG. 10, the beam splitter 15 is located between the two-dimensional scanning optical system 20 and the beam splitter 13, and the OCT optical system 60 is located in the reflection direction of the beam splitter 15.

The OCT optical system 60 forms a tomographic image of the eye fundus Ef based on data (data detected by a detector 66, described later) obtained by optical scanning. As illustrated in FIG. 11, the OCT optical system 60 includes a light source 61, an optical coupler 62, collimate lens units 63 and 64, a reference mirror 65, and the detector 66. The OCT optical system 60 splits low-coherence light L0 output from the light source 61 into reference light LR and signal light LS, and superimposes the reference light LR that has passed through the reference mirror 65 as a reference object and the signal light LS that has passed through the eye fundus Ef as an object to be measured, thereby generating interference light LC. The image forming unit 230d analyzes a signal corresponding to the interference light LC to generate an image of the object to be measured (eye fundus Ef).

The light source 61 includes a broadband light source such as a light-emitting diode (LED), a super luminescent diode (SLD) that outputs the low-coherence light L0, and the like. The low-coherence light L0 has, for example, a near-infrared wavelength and a temporal coherence length of about several tens of micrometers. The low-coherence light L0 output from the light source 61 has a wavelength longer than that of laser light output from the light source 11a of the irradiation optical system 10, for example, in a range of about 800 nm to 900 nm.

The low-coherence light L0 output from the light source 61 is guided to the optical coupler 62 via, for example, an optical fiber made of a single-mode fiber or a polarization-preserving fiber. The optical coupler 62 splits the low-coherence light L0 into the reference light LR and the signal light LS. While the optical coupler 62 has the functions of coupling light (coupler) as well as splitting light (splitter), it is herein referred to as "optical coupler".

The reference light LR generated by the optical coupler 62 is guided by an optical fiber made of a single-mode fiber or the like and is emitted from the end surface of the optical fiber. The reference light LR is then collimated by the collimate lens unit 63, and reflected by the reference mirror 65. The reference light LR reflected by the reference mirror 65 is converged at the end surface of the optical fiber by the collimate lens unit 63. The reference light LR thus converged is guided to the optical coupler 62 via the optical fiber.

The reference mirror 65 is configured to be movable in the optical axis direction (directions indicated by arrow h in FIG. 11) in the traveling direction of the reference light LR. This secures the optical path length for the reference light LR according to the axial length of the subject's eye E. The reference mirror 65 is moved by a drive mechanism (not illustrated) including an actuator.

The signal light LS generated by the optical coupler 62 is guided by an optical fiber made of a single-mode fiber or the like and is emitted from the end surface of the optical fiber. The end surface of the optical fiber is located in a position optically conjugate to the eye fundus Ef of the subject's eye E. The signal light LS is then collimated by the collimate lens unit 64, and reflected by the beam splitter 15 toward the two-dimensional scanning optical system 20.

As described above, the signal light LS directed to the two-dimensional scanning optical system 20 is guided to the subject's eye position. The signal light LS incident on the subject's eye E positioned at the subject's eye position is focused on the eye fundus Ef (retina) and reflected. At this point, the signal light LS is not only reflected by the surface of the eye fundus Ef, but it also reaches the deep area of the eye fundus Ef and is scattered on the refractive index boundary. Accordingly, the signal light LS that has passed though the eye fundus Ef contains information that reflects the surface form of the eye fundus Ef and information that reflects backward scattering on the refractive index boundary of the deep fundus tissue. The light may be simply referred to as "fundus reflection light of the signal light LS".

The fundus reflection light of the signal light LS travels back the above path to the beam splitter 15. Having been reflected by the beam splitter 15, the fundus reflection light of the signal light LS is incident on the OCT optical system 60 and converged on the end surface of the optical fiber by the collimate lens unit 64, and returns to the optical coupler 62. The optical coupler 62 superimposes the signal light LS and the reference light LR reflected by the reference mirror 65, thereby generating the interference light LC. The interference light LC is guided to the detector 66 via an optical fiber made of a single-mode fiber or the like.

While, in the embodiment, a Michelson interferometer is used as described above, any interferometer such as, for example, a Mach-Zehnder interferometer may be used as appropriate.

The detector 66 includes, for example, a collimate lens, a diffraction grating, an imaging lens, and a charge coupled device (CCD). The interference light LC incident on the detector 66 is collimated by the collimate lens, and is dispersed (spectrally resolved) by the diffraction grating. The interference light LC thus dispersed is then focused on the imaging surface of the CCD by the imaging lens. Having received the interference light LC, the CCD converts it to an electrical detection signal, and outputs it to the image forming unit 230d.

Although the OCT optical system 60 is described referring to FIG. 11 as being of spectral-domain type, it may be of swept source type. In this case, the light source 61 is provided with a wavelength-swept light source, and also the detector 66 is provided with a photodetector instead of the optical member that spectrally resolves the interference light LC. The detector 66 sends a detection result (detection signal) obtained by the photodetector to the image forming unit 230d. The image forming unit 230d performs the Fourier transform or the like of the spectral distribution based on the detection result with respect to each A-scan line, for example, to form a tomographic image. Regarding the configuration of the OCT optical system 60, any known technology may be applied according to the type of OCT.

Configuration Example of Processing System

Figure 12:
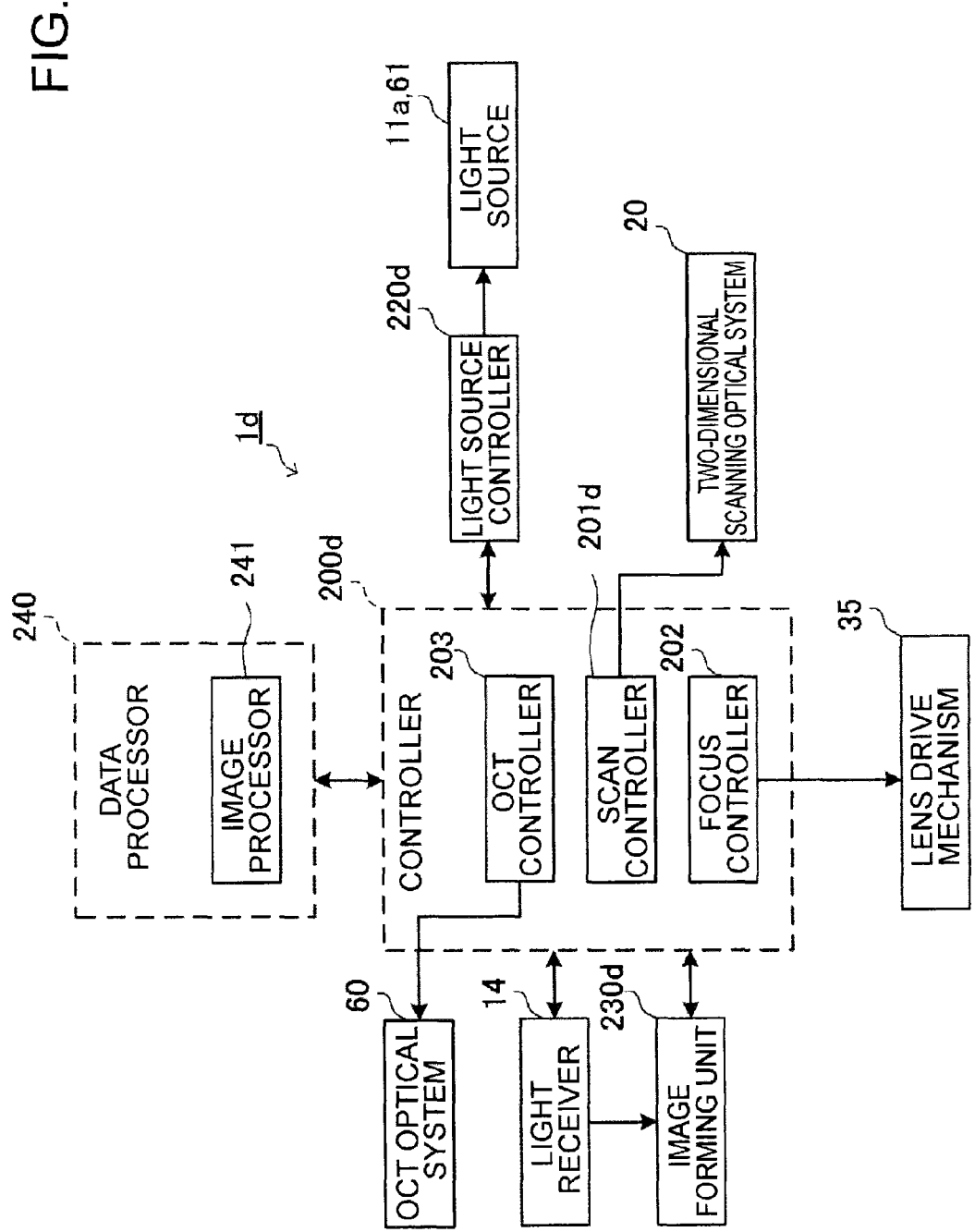
FIG. 12 is a functional block diagram illustrating an example of the configuration of the ophthalmologic apparatus of the fifth embodiment.

FIG. 12 is a functional block diagram illustrating an example of the configuration of the processing system of the ophthalmologic apparatus 1d. FIG. 12 dose not illustrate parts not necessary for explaining the operation of this embodiment. In FIG. 12, like parts are designated by like reference numerals as in FIGS. 4 and 9 to 11 and repetitious description of such parts may not be provided.

The controller 200d performs various types of processes as well as controlling each unit of the apparatus. The controller 200d includes a scan controller 201d, the focus controller 202, and an OCT controller 203.

As with the scan controller 201, the scan controller 201d controls the two-dimensional scanning optical system 20, and thereby two-dimensionally scans laser light. Specifically, for example, the scan controller 201d rotates the polygon mirror 21 about the first rotation axis P1, and also rotates the rotating mirror 23 about the second rotation axis P2 along with the rotation of the polygon mirror 21.

The OCT controller 203 controls the drive mechanism (not illustrated) to move the reference mirror 65 to a desired position. Specifically, for example, the OCT controller 203 moves the reference mirror 65 to achieve an optical path length according to an instruction given by a user through the user interface 250. That is, in response to an instruction of a user input through the user interface 250, the OCT controller 203 sends a control signal to the actuator of the drive mechanism. The actuator generates drive force according to the control signal, and moves the reference mirror 65 to a desired position.

The light source controller 220d controls the light sources 11a and 61 under the control of the controller 200d. The light source controller 220d controls the light sources 11a and 61 by controlling power supplied from the power supply 210, for example. The light source controller 220d includes, for example, a microprocessor and a storage device. The light source controller 220d may also include a dedicated hardware.

The image forming unit 230d generates image data based on a light-receiving signal fed from the light receiving element 14c and a pixel location signal fed from the controller 200d. The image data corresponds to the front image of the eye fundus Ef. The image forming unit 230d analyzes a signal corresponding to the interference light LC to generate an image of the object to be measured (eye fundus Ef). The image forming unit 230d includes, for example, a microprocessor and a storage device. The image forming unit 230d may further include a dedicated hardware.

In the fifth embodiment, the optical system 100d may include the irradiation optical system 10 and the OCT optical system 60, and have a configuration illustrated in FIG. 10 without the fixation optical system 50 in the optical system 100d.

The ophthalmologic apparatus 1d of the fifth embodiment operates in the same manner as in the third embodiment, and therefore the description is not repeated here.

Action and Effects

Action and Effects of the ophthalmologic apparatus 1d of this embodiment will now be described.

The ophthalmologic apparatus 1 d includes the two-dimensional scanning optical system 20, the refractive optical system 30, and the concave mirror 40. The ophthalmologic apparatus 1d may further include the second optical system and the beam splitter 15 (second beam splitter). The second optical system is used to illuminate the subject's eye E with light. The beam splitter 15 is located between the light source 11a and the two-dimensional scanning optical system 20. The beam splitter 15 combines the optical path of light from the light source 11a with that of the second optical system. The second optical system may include the OCT optical system 60 for acquiring an image of the subject's eye E by OCT.

With the ophthalmologic apparatus 1d as described above, light scanned by the two-dimensional scanning optical system 20 can be emitted from the refractive optical system 30 in wide angles toward the reflective surface of the concave mirror 40. Thus, in the exit focus of the concave mirror 40 (the second focus F2), the light can be emitted to the subject's eye E in a range of (2×θ) degrees. Accordingly, the front image and tomographic image of the eye fundus Ef can be acquired in a wide view with a compact apparatus having one concave mirror. Besides, since the front image and tomographic image of the eye fundus Ef are acquired by the shared use of the two-dimensional scanning optical system 20, the cost and size of the apparatus can be reduced.

Further, the ophthalmologic apparatus 1d is capable of acquiring each of the front image and tomographic image of the eye fundus Ef at any timing. Therefore, for example, the front image and tomographic image of the eye fundus Ef can be acquired in parallel at the same time.

Sixth Embodiment

In the fifth embodiment, an example is described in which the two-dimensional scanning optical system 20 is shared by optical systems for acquiring the front image of the eye fundus Ef and for acquiring the tomographic image thereof. However, this is by way of example and not by way of limitation. In a sixth embodiment, an example is described in which optical systems for acquiring the front image of the eye fundus Ef and for acquiring the tomographic image thereof each have a two-dimensional scanning optical system.

The ophthalmologic apparatus of the sixth embodiment is of basically the same configuration as that of the fifth embodiment except for the optical system. The optical system of the sixth embodiment is of a similar configuration to the optical system 100a of the second embodiment except for the presence of the fixation optical system 50 and the OCT optical system 60. The ophthalmologic apparatus of the sixth embodiment is described below mainly about the differences from the fifth embodiment. The optical system of the sixth embodiment is described below mainly about the differences from the second embodiment.

Figure 13:
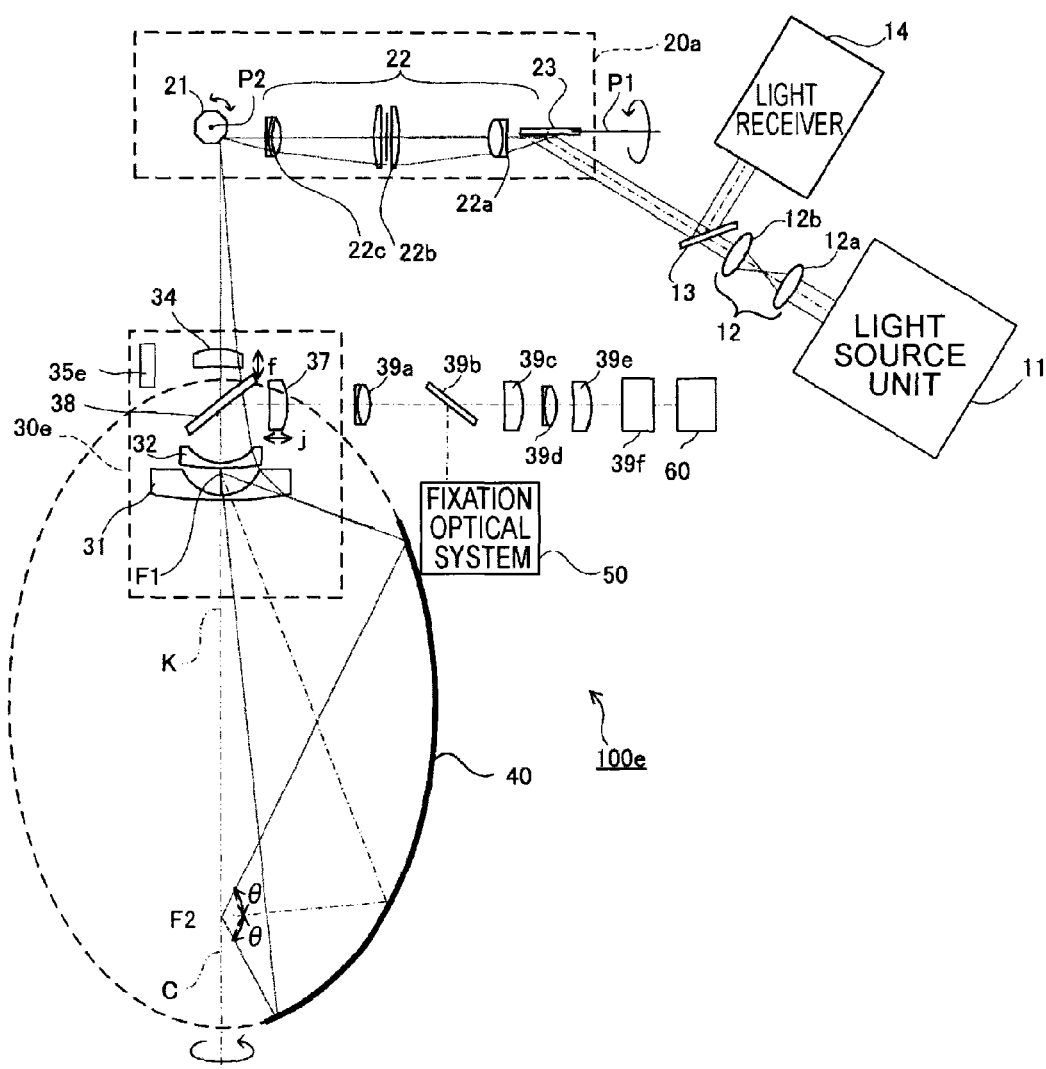
FIG. 13 is a schematic diagram illustrating an example of the configuration of an optical system according to a sixth embodiment.

FIG. 13 is a schematic diagram illustrating an example of the configuration of an optical system according to the sixth embodiment. In FIG. 13, like parts are designated by like reference numerals as in FIG. 5 and repetitious description of such parts may not be provided.

An optical system 100e of the sixth embodiment is different from the optical system 100a of the second embodiment in a refractive optical system 30e, the fixation optical system 50, the OCT optical system 60, and the like. The refractive optical system 30e is provided in place of the refractive optical system 30.

The refractive optical system 30e includes the meniscus lenses 31 and 32 each having a convex surface that faces the object side, the meniscus lenses 34 and 37 each having a convex surface that faces the image side, a half mirror 38, and a lens drive mechanism 35e. The half mirror 38 is located between the meniscus lenses 32 and 34 and also between the meniscus lenses 32 and 37. The meniscus lens 34 is located in the transmission direction of the half mirror 38. The meniscus lens 37 is located in the reflection direction of the half mirror 38.

The meniscus lens 34 has a positive refractive power. Among the optical elements that constitute the refractive optical system 30e, the meniscus lens 34 is arranged in a position optically closest to the two-dimensional scanning optical system 20a. Laser light two-dimensionally scanned by the two-dimensional scanning optical system 20a is incident on the convex surface of the meniscus lens 34.

The meniscus lens 37 has a positive refractive power. Among the optical elements that constitute the refractive optical system 30e, the meniscus lens 37 is arranged in a position optically closest to the fixation optical system 50 and the OCT optical system 60. The meniscus lens 37 is configured to be movable in the optical axis direction (directions indicated by arrow j in FIG. 13) in the reflection direction of the half mirror 38.

The lens drive mechanism 35e moves the meniscus lens 34 in the optical axis direction (directions indicated by arrow f in FIG. 13) in the transmission direction of the half mirror 38. In addition, the lens drive mechanism 35e moves the meniscus lens 37 in the optical axis direction (directions indicated by arrow j in FIG. 13) in the reflection direction of the half mirror 38. The lens drive mechanism 35e includes one or more actuators that generate drive force to move the meniscus lenses 34 and 37. Upon receipt of a control signal from the controller (focus controller) of this embodiment, the actuator(s) generates drive force according to the control signal. The drive force is transmitted to either or both the meniscus lenses 34 and 37 via a drive force transmitting mechanism (not illustrated) to move each of them to a position indicated by the control signal. This enables the optical path length to be changeable, thereby implementing the focusing function.

The optical system 100e includes a lens 39a, a beam splitter 39b, a field lens 39c, an imaging lens 39d, a relay lens 39e, a two-dimensional scanner 39f, the fixation optical system 50, and the OCT optical system 60. The lens 39a, the beam splitter 39b, the field lens 39c, the imaging lens 39d, the relay lens 39e, the two-dimensional scanner 39f, and the OCT optical system 60 are arranged in this order from the refractive optical system 30e on the optical axis of the meniscus lens 37. The fixation optical system 50 is located in the reflection direction of the beam splitter 39b. The fixation optical system 50 has a configuration as illustrated in FIG. 5. The two-dimensional scanner 39f may be, for example, a pair of galvanomirrors, the rotation axes of which are perpendicular to each other. The reflective surface of each of the galvanomirrors is located in a position optically conjugate to the pupil of the subject's eye E. The two-dimensional scanner 39f operates under the control of the OCT controller of the controller.

The light output from the LCD 53 of the fixation optical system 50 travels through the plano-convex lens 52 and the lens 51, and reflected on the reflective surface of the beam splitter 39b. The light is then converged by the lens 39a and passes through the meniscus lens 37 to be reflected on the half mirror 38. After that, the light is deflected by the meniscus lenses 32 and 31, and thereby projected on the eye fundus Ef.

The signal light LS emitted from the OCT optical system 60 is two-dimensionally scanned by the two-dimensional scanner 39f, and travels through the relay lens 39e, the imaging lens 39d, and the field lens 39c, and is incident on the beam splitter 39b. Having passed through the beam splitter 39b, the signal light LS is converged by the lens 39a, and passes through the meniscus lens 37 to be reflected on the half mirror 38. Thus, the signal light LS is guided to the subject's eye position as described above. The signal light LS incident on the subject's eye E at the subject's eye position is focused on the eye fundus (retina) Ef and is reflected.

The fundus reflection light of the signal light LS travels back the above path to be incident on the OCT optical system 60. Having been converged at the end surface of the optical fiber by the collimate lens unit 64, the fundus reflection light of the signal light LS returns to the optical coupler 62. The optical coupler 62 superimposes the signal light LS and the reference light LR reflected by the reference mirror 65, thereby generating the interference light LC. The interference light LC is guided to the detector 66 via an optical fiber made of a single-mode fiber or the like.

The ophthalmologic apparatus of the sixth embodiment operates in the same manner as in the fifth embodiment, and therefore the description is not repeated here. Incidentally, in the FIG. 13, the beam splitter 39b may be located between the field lens 39c and the imaging lens 39d.

Action and Effects

Action and Effects of the ophthalmologic apparatus of this embodiment are described.

The ophthalmologic apparatus of this embodiment includes the two-dimensional scanning optical system 20a, the refractive optical system 30e, and the concave mirror 40. The refractive optical system 30e deflects light deflected by the two-dimensional scanning optical system 20a in the second angle range that is wider than the first angle range. The refractive optical system 30e is arranged such that its exit-side optical axis K substantially coincides with the rotational symmetry axis C of the rotational symmetry surface including the reflective surface of the concave mirror 40. The pupil location (entrance or exit pupil location) in the refractive optical system 30e and the exit focus of the concave mirror 40 (the second focus F2) are located at optically conjugate positions or in the vicinity of the positions. The exit focus (the second focus F2) is located at the subject's eye position.

The refractive optical system 30e may include the meniscus lens 31 (first optical element) and the meniscus lens 34 (second optical element). The meniscus lens 31 is arranged in a position optically closest to the concave mirror 40. The meniscus lens 34 is arranged in a position optically closest to the two-dimensional scanning optical system 20a. The meniscus lens 34 is configured to be movable in the optical axis direction of the refractive optical system 30e.

The ophthalmologic apparatus may further include the first optical system and the half mirror 38 (beam splitter). The first optical system is used to illuminate the subject's eye E with light. The half mirror 38 is located between the meniscus lens 31 (first optical element) and the meniscus lens 34 (second optical element). The half mirror 38 combines the optical path of the refractive optical system 30e with that of the first optical system. The first optical system may include the fixation optical system 50 for projecting a fixation target on the subject's eye E. The first optical system may further include the OCT optical system 60 for acquiring an image of the subject's eye E by OCT.

With the ophthalmologic apparatus as described above, light scanned by the two-dimensional scanning optical system 20a can be emitted from the refractive optical system 30e in wide angles toward the reflective surface of the concave mirror 40. Thus, in the exit focus of the concave mirror 40 (the second focus F2), the light can be emitted to the subject's eye E in a range of (2×θ) degrees. Accordingly, the front image of the eye fundus Ef can be acquired in a wide view with a compact apparatus having one concave mirror. Besides, since the optical path of the refractive optical system 30e is combined with that of the fixation optical system 50 and the OCT optical system 60 by the half mirror 38, the front image and tomographic image of the eye fundus Ef can be acquired in a wide view while a fixation target is being projected to a desired position on the eye fundus Ef.

Seventh Embodiment

In the sixth embodiment, an example is described in which the fixation optical system 50 is located in the reflection direction of the half mirror 38 in the refractive optical system 30e. However, this is by way of example and not by way of limitation. In a seventh embodiment, an example is described in which the fixation optical system 50 is located in the transmission direction of the half mirror 38, while the OCT optical system 60 is located in the reflection direction thereof.

The ophthalmologic apparatus of the seventh embodiment is of basically the same configuration as that of the sixth embodiment except for the optical system. The optical system of the seventh embodiment is of a similar configuration to the optical system 100c of the fourth embodiment except for the presence of the OCT optical system 60. The ophthalmologic apparatus of the seventh embodiment is described below mainly about the differences from the sixth embodiment. The optical system of the seventh embodiment is described below mainly about the differences from the fourth embodiment.

Figure 14:
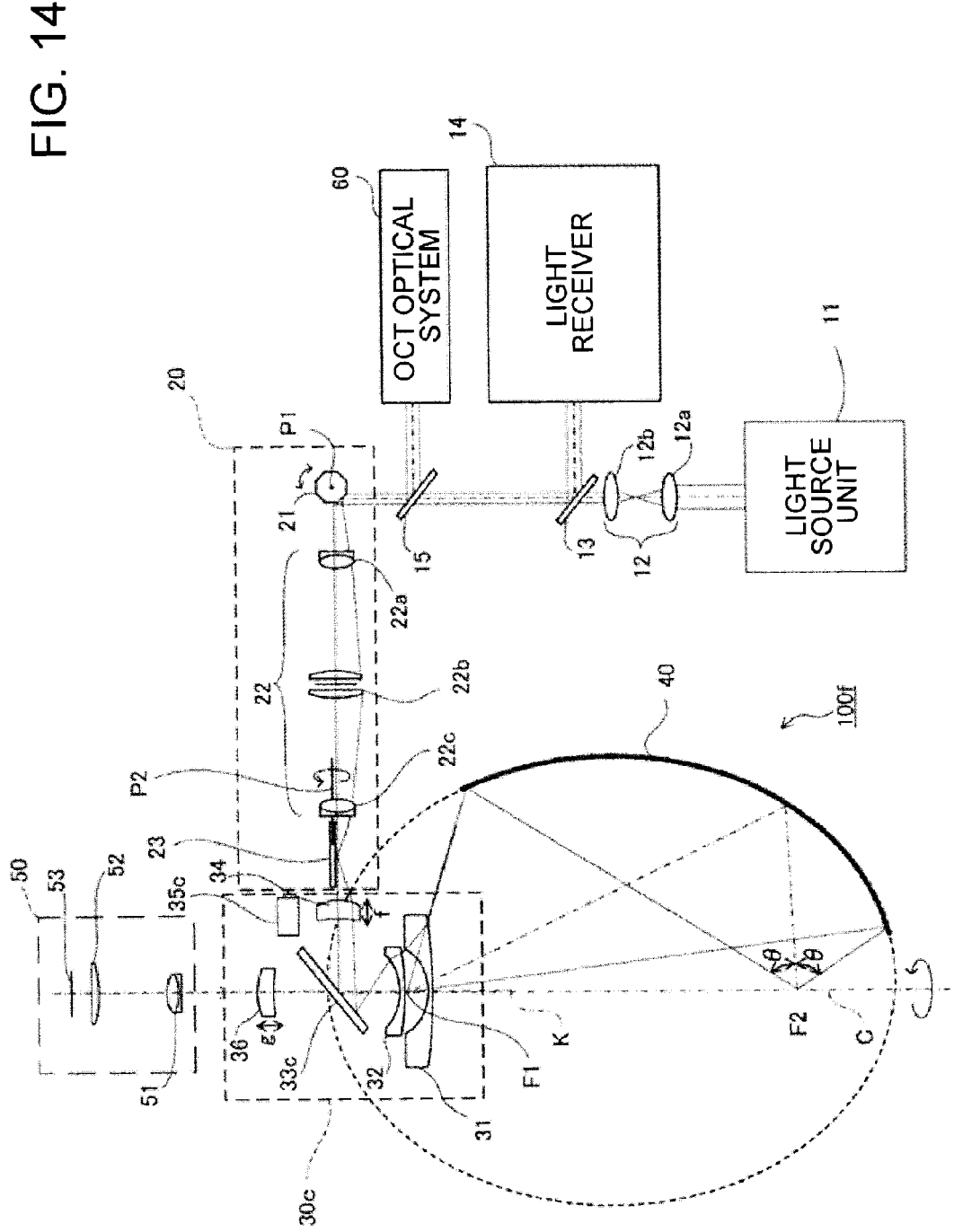
FIG. 14 is a schematic diagram illustrating an example of the configuration of an optical system according to a seventh embodiment.

FIG. 14 is a schematic diagram illustrating an example of the configuration of an optical system according to the seventh embodiment. In FIG. 14, like parts are designated by like reference numerals as in FIG. 8 and repetitious description of such parts may not be provided.

An optical system 100f of the seventh embodiment is different from the optical system 100c of the fourth embodiment in the presence of the beam splitter 15 and the OCT optical system 60. The beam splitter 15 is located between the beam expander 12 and the two-dimensional scanning optical system 20. The OCT optical system 60 is located in the reflection direction of the beam splitter 15.

The light output from the LCD 53 of the fixation optical system 50 travels through the plano-convex lens 52 and the lens 51, and is deflected by the refractive optical system 30c and thereby projected on the eye fundus Ef. The return light from the subject's eye E is reflected in the reflection direction of the half mirror 33c, and received by the light receiver 14 as in the first embodiment.

The signal light LS emitted from the OCT optical system 60 is reflected by the beam splitter 15 and directed toward the two-dimensional scanning optical system 20.

As described above, the signal light LS directed to the two-dimensional scanning optical system 20 is guided to the subject's eye position. The signal light LS incident on the subject's eye E positioned at the subject's eye position is focused on the eye fundus Ef (retina) and reflected.

The fundus reflection light of the signal light LS travels back the above path to be incident on the OCT optical system 60. Having been converged at the end surface of the optical fiber by the collimate lens unit 64, the fundus reflection light of the signal light LS returns to the optical coupler 62. The optical coupler 62 superimposes the signal light LS and the reference light LR reflected by the reference mirror 65, thereby generating the interference light LC. The interference light LC is guided to the detector 66 via an optical fiber made of a single-mode fiber or the like.

The ophthalmologic apparatus of the seventh embodiment operates in the same manner as in the sixth embodiment, and therefore the description is not repeated here.

Action and Effects

Action and Effects of the ophthalmologic apparatus of this embodiment are described.

The ophthalmologic apparatus of this embodiment includes the two-dimensional scanning optical system 20, the refractive optical system 30c, and the concave mirror 40. The ophthalmologic apparatus may further include the second optical system and the beam splitter 15. The second optical system is used to illuminate the subject's eye E with light. The beam splitter 15 is located between the light source 11a and the two-dimensional scanning optical system 20. The beam splitter 15 combines the optical path of light from the light source 11a with that of the second optical system. The second optical system may include the OCT optical system for acquiring an image of the subject's eye E by OCT.

With the ophthalmologic apparatus as described above, light scanned by the two-dimensional scanning optical system 20 can be emitted from the refractive optical system 30c in wide angles toward the reflective surface of the concave mirror 40. Thus, in the exit focus of the concave mirror 40 (the second focus F2), the light can be emitted to the subject's eye E in a range of (2×θ) degrees. Accordingly, the front image and tomographic image of the eye fundus Ef can be acquired in a wide view while a fixation target is being projected to a desired position on the eye fundus Ef with a compact apparatus having one concave mirror Eighth Embodiment In the first to seventh embodiments, examples are described in which the concave mirror 40 is an ellipsoidal mirror. However, this is by way of example and not by way of limitation. In an eighth embodiment, an example is described in which the concave mirror has not an ellipsoidal but an adjustable reflective surface.

The ophthalmologic apparatus of the eighth embodiment is of basically the same configuration as that of the first embodiment except for the concave mirror. The ophthalmologic apparatus of the eighth embodiment is described below mainly about the differences from the first embodiment.

Figure 15:
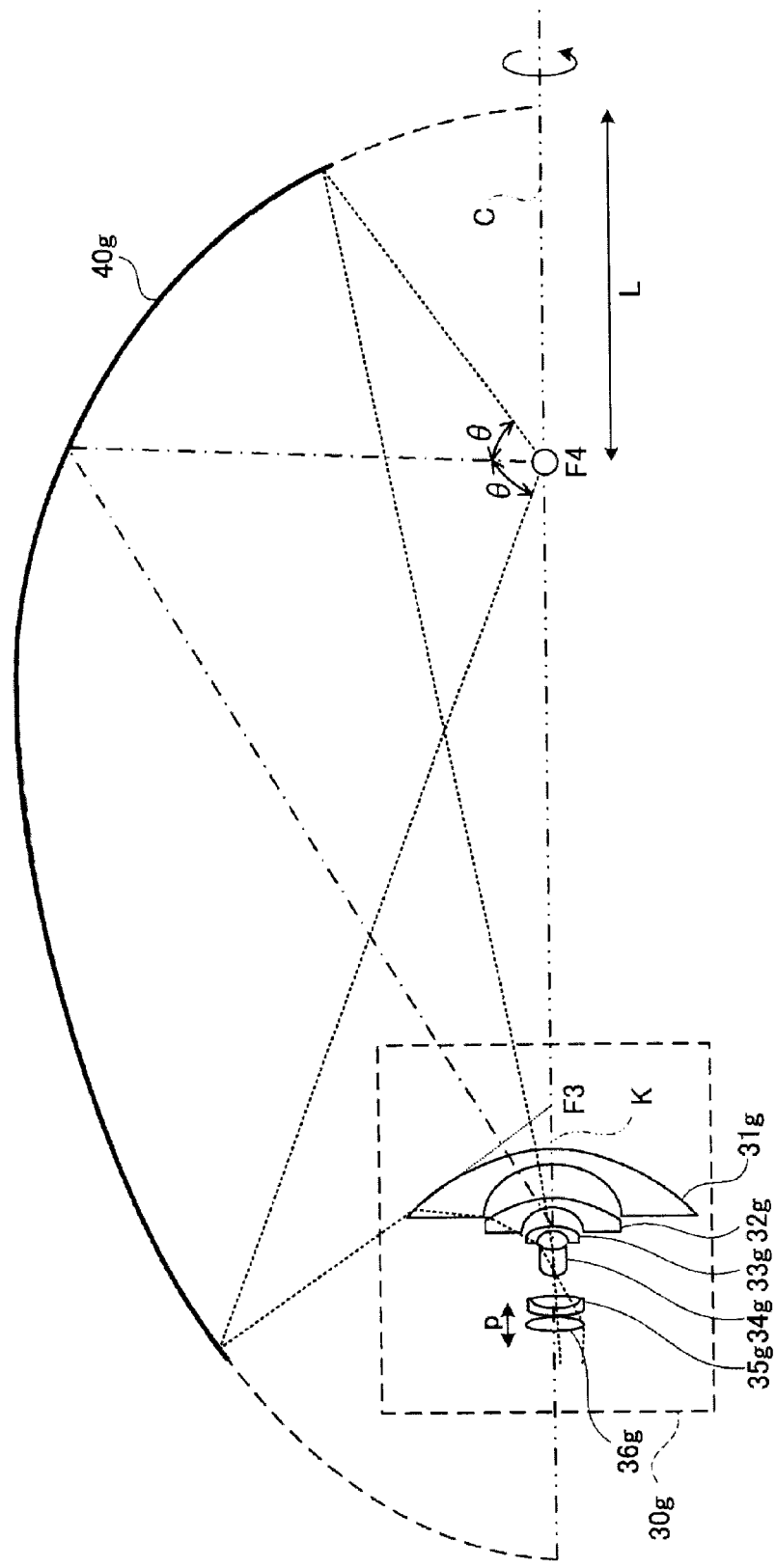
FIG. 15 is a schematic diagram illustrating an example of the configuration of an optical system according to an eighth embodiment.

FIG. 15 is a schematic diagram illustrating an example of the configuration of an optical system according to the eighth embodiment. In FIG. 15, like parts are designated by like reference numerals as in FIG. 1 and repetitious description of such parts may not be provided.

The irradiation optical system 10 of the eighth embodiment includes the light source unit 11, the beam expander 12, the beam splitter 13, the light receiver 14, the two-dimensional scanning optical system 20, a refractive optical system 30g, and a concave mirror 40g. FIG. 15 illustrates the refractive optical system 30g and the concave mirror 40g without the illustration of the light source unit 11, the beam expander 12, the beam splitter 13, the light receiver 14, and the two-dimensional scanning optical system 20, As with the refractive optical system 30, the refractive optical system 30g deflects light deflected by the two-dimensional scanning optical system 20 in the second angle range that is wider than the first angle range. The second angle range may be a half-angle of view of 30 degrees or more. That is, the refractive optical system 30g is a wide-angle optical system. Preferably, the second angle range is a half-angle of view of 45 degrees or more. In this case, the refractive optical system 30g is a super wide-angle optical system. The refractive optical system 30g is arranged such that its exit-side optical axis K substantially coincides with the rotational symmetry axis C of the concave mirror 40g.

The refractive optical system 30g includes meniscus lenses 31g, 32g, and 33g each having a convex surface that faces the object side (the concave mirror 40g side in FIG. 15), a meniscus lens 34g having a convex surface that faces the image side (the two-dimensional scanning optical system 20 side in FIG. 15), a laminated lens 35g, and a biconvex lens 36g. The meniscus lenses 31g, 32g, 33g, and 34g, the laminated lens 35g, and the biconvex lens 36g are arranged in this order from the object side to the image side on the optical axis in the refractive optical system 30g.

In the refractive optical system 30g, the reflective mirror 33 of FIG. 2, the half mirror 33c of FIG. 8 or 14, and the half mirror 38 of FIG. 13 may be located between the meniscus lens 33g and the laminated lens 35g.

The meniscus lens 31g has a negative refractive power. Among the optical elements that constitute the refractive optical system 30g, the meniscus lens 31g is arranged in a position optically closest to the concave mirror 40g. Since the meniscus lenses 31g, 32g, and 33g having a negative refractive power are arranged in this order from the object side to the image side, the optical power of negative lenses are divided to them, and the refractive optical system 30g can achieve better optical characteristics as a wide-angle optical system.

Among the optical elements that constitute the refractive optical system 30g, the biconvex lens 36g is arranged in a position optically closest to the two-dimensional scanning optical system 20. Laser light two-dimensionally scanned by the two-dimensional scanning optical system 20 is incident on an image-side surface of the biconvex lens 36g.

The lens drive mechanism 35 moves the biconvex lens 36g in the optical axis direction (directions indicated by arrow p in FIG. 15) of the refractive optical system 30g. In other words, the biconvex lens 36g is configured to be movable in the optical axis direction of the refractive optical system 30g. The lens drive mechanism 35 includes an actuator that generates drive force to move the biconvex lens 36g. Upon receipt of a control signal from a controller (not illustrated), the actuator generates drive force according to the control signal. The drive force is transmitted to the biconvex lens 36g via a drive force transmitting mechanism (not illustrated) to move the biconvex lens 36g to a position indicated by the control signal, thereby implementing the focusing function. This enables diopter scale correction.

The concave mirror 40g has a reflective surface in at least part of the rotational symmetry surface, and reflects light emitted from the refractive optical system 30g. In this embodiment, the rotational symmetry surface is an adjustable surface. The concave mirror 40g is arranged such that the rotational symmetry axis C of the rotational symmetry surface thereof substantially coincides with the exit-side optical axis K of the refractive optical system 30g. The pupil location (entrance or exit pupil location) F3 in the refractive optical system 30g and the exit focus F4 of the concave mirror 40g are located at optically conjugate positions or in the vicinity of the positions. The exit focus F4 is located at the subject's eye position where the subject's eye E is located. Accordingly, the concave mirror 40g guides light emitted from the refractive optical system 30g to the subject's eye position.

The ophthalmologic apparatus of the eighth embodiment operates in the same manner as in the first embodiment, and therefore the description is not repeated here.

Action and Effects

Action and Effects of the ophthalmologic apparatus of this embodiment are described.

The ophthalmologic apparatus of this embodiment includes the two-dimensional scanning optical system 20, the refractive optical system 30g, and the concave mirror 40g. The two-dimensional scanning optical system 20 deflects light form the light source in the first angle range. The refractive optical system 30g deflects the light deflected by the two-dimensional scanning optical system 20 in the second angle range that is wider than the first angle range. The concave mirror 40g has a reflective surface in at least part of the rotational symmetry surface, and reflects the light emitted from the refractive optical system 30g. The refractive optical system 30g is arranged such that its exit-side optical axis K substantially coincides with the rotational symmetry axis C of the rotational symmetry surface. The pupil location (entrance or exit pupil location) F3 in the refractive optical system 30g and the exit focus F4 of the concave mirror 40g are located at optically conjugate positions or in the vicinity of the positions. The exit focus F4 is located at the subject's eye position.

With the ophthalmologic apparatus as described above, the laser light that has been two-dimensionally deflected by the two-dimensional scanning optical system 20 can be emitted from the refractive optical system 30g in wide angles toward the reflective surface of the concave mirror 40g. However, the pupil aberration tends to increase as the angle gets wider, and the light flux is spread at the exit pupil location (F3) in the refractive optical system 30g. With the concave mirror 40g having an adjustable reflective surface, the pupil aberration can be corrected. Thus, in the exit focus F4 of the concave mirror 40g, the laser light can be emitted to the subject's eye E in a range of (2×θ) degrees. Accordingly, the eye fundus Ef can be observed in a wide view with a compact apparatus having one concave mirror. Besides, since the concave mirror 40g has an adjustable refractive surface, design flexibility is enhanced. This enables, for example, aberration correction with the use of the refractive optical system 30g and the concave mirror 40g, thereby further improving image quality.

Ninth Embodiment

In the ophthalmologic apparatus of the ninth embodiment, the concave mirror is an adjustable surface mirror as in the eighth embodiment. The ophthalmologic apparatus of the ninth embodiment is of basically the same configuration as that of the first embodiment. The ophthalmologic apparatus of the ninth embodiment is described below mainly about the differences from the first embodiment.

Figure 16:
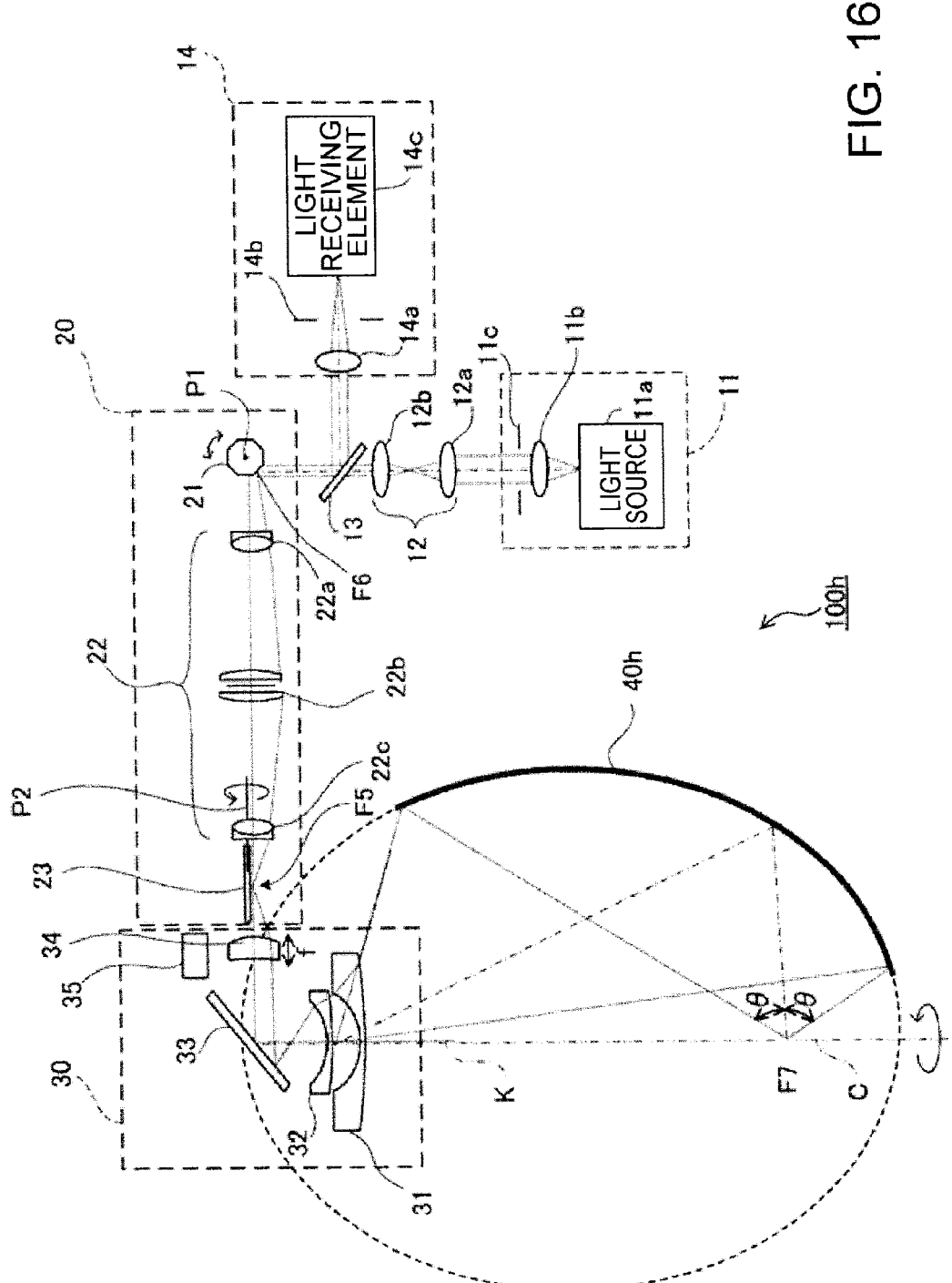
FIG. 16 is a schematic diagram illustrating an example of the configuration of an optical system according to a ninth embodiment.

FIG. 16 is a schematic diagram illustrating an example of the configuration of an optical system according to the ninth embodiment. In FIG. 16, like parts are designated by like reference numerals as in FIG. 1 and repetitious description of such parts may not be provided.

The ophthalmologic apparatus of the ninth embodiment includes a concave mirror 40h. The concave mirror 40h is the same adjustable surface mirror as the concave mirror 40g of the eighth embodiment. In this embodiment, the pupil location on the light source side in the refractive optical system 30 (position F6 on the reflective surface (deflected surface) of the polygon mirror 21) and the exit focus F7 of the concave mirror 40h are located at optically conjugate positions or in the vicinity of the positions. The exit focus F7 is located at the subject's eye position. In FIG. 16, a position F5 on the reflective surface of the rotating mirror 23, the position F6 on the reflective surface of the polygon mirror 21, and the exit focus F7 may be located at optically conjugate positions or in the vicinity of the positions.

Others

With the ophthalmologic apparatus of any of the above embodiments, a beam splitter may be arranged in an arbitrary position.

This enables the irradiation optical system to be combined with a third optical system for illuminating the subject's eye E with light. The beam splitter (third beam splitter) is located between the light source 11a and the first optical element (e.g., the meniscus lens 31). The beam splitter combines the optical path of light from the light source 11a with that of the third optical system. Thus, the front image of the eye fundus Ef can be acquired in a wide view with a compact apparatus having one concave mirror while the subject's eye E is being illuminated by the third optical system.

The configuration of the ophthalmologic apparatus is not limited to the above embodiments.

In the first to ninth embodiments, the ophthalmologic apparatus may include a unit for stimulating the retina. In this case, a stimulated image (the front image and tomographic image of the eye fundus Ef after the retina is stimulated) is compared with a non-stimulated image (the front image and tomographic image of the eye fundus Ef before the retina is stimulated) to check the neural retina function and the like.

The first to ninth embodiments are applicable to an apparatus including an optical system that guides therapeutic laser light.

In the eighth or ninth embodiment, the concave mirror 40g may have a deformable reflective surface. In this case, the position of the exit focus F4 or F7 can be adjusted, and thus the fine adjustment of the image quality and the like can be accomplished.

While preferred embodiments have been illustrated and described, various modifications (alterations, substitutions and adaptations) may be made thereto without departing from the spirit and scope of the claims appended hereto.

The various features of the first to ninth embodiments may be variously combined with some features included and others excluded to suit a variety of different applications.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ophthalmologic apparatus, comprising:
   a two-dimensional scanning optical system configured to deflect light from a light source in a first angle range;
   a refractive optical system configured to deflect the light deflected by the two-dimensional scanning optical system in a second angle range that is wider than the first angle range; and
   a concave mirror including a reflective surface in at least part of a rotational symmetry surface, the concave mirror configured to reflect the light emitted from the refractive optical system, wherein
   an exit-side optical axis of the refractive optical system substantially coincides with a rotational symmetry axis of the rotational symmetry surface,
   pupil location in the refractive optical system and an exit focus of the concave mirror are located at optically conjugate positions or in vicinity of the positions, and
   the exit focus is located at a subject's eye position.

2. The ophthalmologic apparatus of claim 1, further comprising a light receiver configured to receive the light that returns from the subject's eye position through the concave mirror, the refractive optical system, and the two-dimensional scanning optical system in this order.

3. The ophthalmologic apparatus of claim 1, wherein the two-dimensional scanning optical system includes
   a first scanner configured to be rotatable about a first rotation axis, and perform scanning in a first direction by reflecting light form the light source, and
   a second scanner configured to be rotatable about a second rotation axis that is perpendicular to the first rotation axis, and perform scanning in a second direction that is perpendicular to the first direction by reflecting the light scanned by the first scanner.

4. The ophthalmologic apparatus of claim 3, wherein a reflective surface of the first scanner and a reflective surface of the second scanner are located at optically conjugate positions.

5. The ophthalmologic apparatus of claim 3, wherein
   the first scanner and the second scanner are rotating mirrors, and
   rotation axes of the rotating mirrors are arranged substantially in parallel to an optical axis of the two-dimensional scanning optical system.

6. The ophthalmologic apparatus of claim 1, wherein the refractive optical system includes
   a first optical element that is arranged in a position optically closest to the concave mirror, and
   a second optical element that is arranged in a position optically closest to the two-dimensional scanning optical system, and
   the second optical element is configured to be movable in an optical axis direction of the refractive optical system.

7. The ophthalmologic apparatus of claim 6, wherein the refractive optical system further includes a reflector having a reflective surface that is located at intersection of an optical axis of the first optical element and an optical axis of the second optical element.

8. The ophthalmologic apparatus of claim 6, further comprising:
   a first optical system configured to illuminate a subject's eye with light; and
   a first beam splitter located between the first optical element and the second optical element, wherein
   the first beam splitter is configured to combine an optical path of the refractive optical system with an optical path of the first optical system.

9. The ophthalmologic apparatus of claim 8, wherein the first optical system includes a fixation optical system configured to project a fixation target on the subject's eye.

10. The ophthalmologic apparatus of claim 8, wherein the first optical system includes an OCT optical system configured to acquire an image of the subject's eye by optical coherence tomography.

11. The ophthalmologic apparatus of claim 1, further comprising:
    a second optical system configured to illuminate a subject's eye with light; and
    a second beam splitter located between the light source and the two-dimensional scanning optical system, wherein
    the second beam splitter is configured to combine an optical path of the light from the light source with an optical path of the second optical system.

12. The ophthalmologic apparatus of claim 11, wherein the second optical system includes an OCT optical system configured to acquire an image of the subject's eye by optical coherence tomography.

13. The ophthalmologic apparatus of claim 6, further comprising:
    a third optical system configured to illuminate a subject's eye with light; and
    a third beam splitter located between the light source and the first optical element, wherein
    the third beam splitter is configured to combine an optical path of the light from the light source with an optical path of the third optical system.

14. The ophthalmologic apparatus of claim 1, wherein the second angle range is located in a region deviated from the exit-side optical axis.

15. The ophthalmologic apparatus of claim 1, wherein the concave mirror is an ellipsoidal mirror.

16. The ophthalmologic apparatus of claim 15, wherein
    the concave mirror has a first focus and a second focus,
    the first focus is located at the pupil location or in vicinity of the pupil location, and
    the second focus is located at the subject's eye position.

17. The ophthalmologic apparatus of claim 1, wherein the concave mirror is an adjustable surface mirror.

18. The ophthalmologic apparatus of claim 17, wherein the pupil location on a light source side in the refractive optical system and an exit focus of the concave mirror are located at optically conjugate positions or in vicinity of the positions.

19. The ophthalmologic apparatus of claim 1, wherein the second angle range is 30 degrees or more.

* * * * *